US010478652B2

(12) United States Patent
Nzila et al.

(10) Patent No.: US 10,478,652 B2
(45) Date of Patent: Nov. 19, 2019

(54) METHOD FOR BIODEGRADING HIGH MOLECULAR WEIGHT POLYCYCLIC AROMATIC HYDROCARBON PYRENES WITH HALOPHILIC BACTERIA

(71) Applicant: KING FAHD UNIVERSITY OF PETROLEUM AND MINERALS, Dhahran (SA)

(72) Inventors: Alexis Mouanda Nzila, Dhahran (SA); Assad Ahmed Mohammed Al-Thukair, Dhahran (SA); Musa Mohammed Musa Musa, Dhahran (SA); Fitri Budiyanto, Dhahran (SA)

(73) Assignee: King Fadh University of Petroleum and Minerals, Dhahran (SA)

( * ) Notice: Subject to any disclaimer, the term of this patent is extended or adjusted under 35 U.S.C. 154(b) by 0 days.

(21) Appl. No.: 15/843,809

(22) Filed: Dec. 15, 2017

(65) Prior Publication Data

US 2019/0184219 A1 Jun. 20, 2019

(51) Int. Cl.

*A63D 3/02* (2006.01)
*C12R 1/37* (2006.01)
*C02F 3/34* (2006.01)
*B09C 1/10* (2006.01)
*C12R 1/01* (2006.01)
*C12N 1/20* (2006.01)
*C02F 103/06* (2006.01)
*A62D 101/20* (2007.01)
*A62D 3/02* (2007.01)

(52) U.S. Cl.

CPC . *A62D 3/02* (2013.01); *C12R 1/37* (2013.01)

(58) Field of Classification Search

CPC .................................... A62D 3/02; C12R 1/37
See application file for complete search history.

(56) References Cited

FOREIGN PATENT DOCUMENTS

CN 101838616 B 3/2012
CN 101838617 B 7/2012
CN 101838629 B 9/2012
WO WO 03/12390 A2 2/2003
WO WO 03/12390 A3 2/2003

OTHER PUBLICATIONS

Ahmed et al., Elucidating structures of nonalkylated and short-chain alkyl (n<5,(CH2)n) aromatic compounds in crude oils by a combination of ion mobility and ultrahigh-resolution mass spectrometries and theoretical collisional cross-section calculations. ACS., Anal. Chem., 2014, vol. 86: 3300-3307. (Year: 2014).*

Farooqui SM., Aromatic hydrocarbon degradation by haloalkaliphilic and metal reducing bacteria. Ph.D., Thesis, Sep. 2013, Griffith Univ., Queensland, Australia, pp. 1-317 (Year: 2013).*

Poli et al., *Halomonas smyrnensis* sp. nov., a moderately halophilic, exopolysaccharide-producing bacterium. Int.. J. Syst. Evol. Microbiol., 2013, vol. 63: 10-18. (Year: 2013).*

Wang et al., *Halomonas shengliensis* sp. nov., a moderately halophilic, denitrifying, crude-oil-utilizing bacterium. Int.. J. Syst. Evol. Microbiol., 2007, vol. 57: 1222-1226. (Year: 2007).*

Budiyanto et al., Characterzation of halophilic bacteria capable of efficiently biodegrading the high-molecular-weight polycyclic aromatic hydrocarbon pyrene. Environ. Eng. Sci., 2018, Vo. 35(6): 616-626. (Year: 2018).*

S. Mnif, et al., "Isolation and characterization of *Halomonas* sp. strain C2SS100, a hydrocarbon-degrading bacterium under hypersaline conditions", Journal of Applied Microbiology, vol. 107, No. 3, 2009, 785-794.

Robert M. W. Ferguson, et al., "The Variable Influence of Dispersant or Degradation of Oil Hydrocarbons in Subarctic Deep-Sea Sediments at Low Temperatures (0-5° C.)", Scientific Reports, vol. 7, Article No. 2253, 2017, pp. 1-13.

Baisuo Zhao, et al., "*Halomonas xianhensis* sp. nov., a moderately halophilic bacterium isolated from a saline soil contaminated with crude oil", International Journal of Systematic and Evolutionary Microbiology, vol. 62, Part 1, Jan. 2012, pp. 173-178.

* cited by examiner

*Primary Examiner* — Ganapathirama Raghu
(74) *Attorney, Agent, or Firm* — Oblon, McClelland, Maier & Neustadt, L.L.P.

(57) ABSTRACT

A method and composition for biodegrading or bioremediating a pyrene or other polycyclic aromatic hydrocarbon ("PAH") with one or more bacteria of the genus *Halomonas* or *Idiomarina*. Bacterial strains useful for degrading or remediating pyrenes and other polycyclic aromatic hydrocarbons.

19 Claims, 11 Drawing Sheets

Figure 1B:
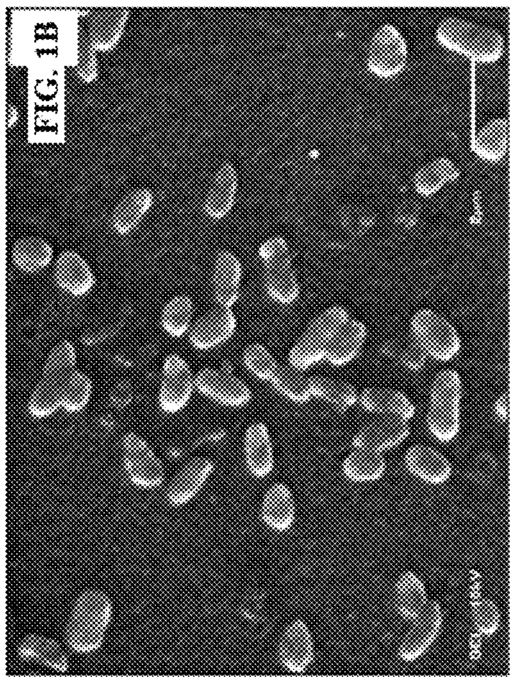

Specification includes a Sequence Listing.

FIG. 11

| Isolate | Gram staining | Light microscopy | | | SEM | NCBI Reference |
|---|---|---|---|---|---|---|
| | | Form | Elevation | Margin | (L x W) µm | |
| *Idiomarina piscisalsi* (10 PY 1A)* | Negative | Circular | Flat | Entire | 4.07 x 0.52 | KU308250.1 Genome="*GCA_002211765.1*" |
| *Halomonas shengliensis* (10 PY 2B) | Negative | Punctiform | Convex | Entire | 0.96 x 0.64 | KU308251.1 |
| *Halomonas smyrnensis* (20 PY 1A) | Negative | Circular | Flat | Entire | 1.53 x 0.75 | KU308252.1 |
| Halomonas xianhensis (A1)** | Negative | Circular | convex | NA | 1.2–1.4x 0.5–0.6 | GI: 636559956 |

METHOD FOR BIODEGRADING HIGH MOLECULAR WEIGHT POLYCYCLIC AROMATIC HYDROCARBON PYRENES WITH HALOPHILIC BACTERIA

REFERENCE TO A SEQUENCE LISTING

In accordance with 37 CFR § 1.52(e)(5), the present specification makes reference to a Sequence Listing which is submitted electronically as a .txt file named "508696US_Sequence_Listing_ST25.txt". The .txt file was generated on Dec. 12, 2017 and is 11 kb in size. The entire contents of the Sequence Listing are herein incorporated by reference.

STATEMENT REGARDING PRIOR DISCLOSURES BY THE INVENTOR(S)

Aspects of this technology are described in Fitri, et al., Environmental Engineering Science. November 2017, ahead of print. Hypertext transfer protocol available at://_doi.org/10.1089/ees.2017.0244, Characterization of Halophilic Bacteria Capable of Efficiently Biodegrading the High-Molecular-Weight Polycyclic Aromatic Hydrocarbon Pyrene (incorporated by reference).

BACKGROUND OF THE INVENTION

Field of the Invention

A method for biodegrading or bioremediating contaminant or waste product containing a pyrene or other polycyclic aromatic hydrocarbon ("PAH") by contacting it with one or more bacteria of the genus *Halomonas* or *Idiomarina.*

Description of Related Art

Fossil oil remains the main energy source that drives world industrial activities. During the extraction of fossil oil and natural gas, large amounts of reservoir water, also known as "produced water" (PW), are generated. As oil content in wells is depleted, the volume of this PW increases; Fakhru'l-Razi, et al., 2009, and about three liters of PW are generated for every liter of produced oil or gas (Fakhru'l-Razi, et al., 2009). Thus, almost a quarter billion of barrels of PW are generated daily in the world, representing 80 million barrels of oil (Fakhru'l-Razi, et al., 2009). Most of the PW is re-injected into the reservoirs to enhance oil recovery but around 5-10% is released on surface ground or into surface waters, representing a staggering volume of almost 100 million liters daily. Being a petroleum waste, PW is contaminated with various pollutants, among them are polycyclic aromatic compounds (PAHs), including naphthalene (NAPH), anthracene (ANT), phenanthrene (PHEN), and pyrene (PYR), among others (Fakhru'l-Razi, et al., 2009). High molecular weight polycyclic aromatic hydrocarbons (HMW PAHs), including PYR, are sparingly soluble in water, which makes them recalcitrant to degradation (A. Nzila, 2013; Seo, Keum, & Li, 2009). These HMW PAHs are associated with adverse environmental effects, affecting both marine flora and human health (Bostrom, et al., 2002). Moreover, PW is characterized by its high salinity that can reach up to more than 30% NaCl, which reduces further the solubility of HMW PAHs (Fakhru'l-Razi, et al.). Because of the high toxicity of HMW PAHs (Bostrom, et al., 2002; Verma, Pink, Rettenmeier, & Schmitz-Spanke, 2012), PW treatment is recommended prior to its release in the environment.

Several approaches to remove pollutants from PW have been evaluated including physical approaches such as adsorption, dissolved air precipitation, evaporation, electrodialysis, sand filtration, and usage of membranes as well as chemical approaches such as precipitation (as a result of chemical reactions), oxidation, photocatalysis and electrochemical approaches, among others (dos Santos, Bezerra Rocha, de Araujo, de Moura, & Martinez-Huitle, 2014; Fakhru'l-Razi, et al., 2009; Munirasu, Haija, & Banat, 2016).

Biodegradation represents an attractive approach to treat PW. It exploits the ability of microorganisms to grow by using pollutants as the sole source of carbon, leading to their removal. This approach is even improved by coupling with bioaugmentation, which involves the addition of efficient microorganisms into a microbial community in an effort to improve the efficiency of natural bacterial community to biodegrade pollutants. Biological approaches, unlike physical and chemical ones, are cost effective and environmentally benign (Alexis Nzila, Razzak, & Zhu, 2016). As stated earlier, salinity levels in PW are generally high, thus, halophilic microorganisms are needed to remove pollutants in this environment. Few studies have reported on the removal of organic pollutants from PW by biodegradation (Beyer & Palmer, 1979; Fathepure, 2014; Martins & Peixoto, 2012).

The coastal line of the Arabian Gulf is heavily involved in oil exploitation and transportation and thus is one of the most exposed areas to oil contamination (Abed, Al-Thukair, & de Beer, 2006). This area is also characterized by high temperature and high salinity and could be a potential source microorganisms that degrade PHAs and that can be used for cleaning PW.

Mnif, et al., J. Appl. Microbiol. 107 (2009) 785-794, reported isolation of a *Halomonas* bacteria strain that could degrade some aliphatic hydrocarbons in crude oil and Ferguson, et al., Scientific Reports 7:2253 (2017) describes microbial degradation of petroleum hydrocarbons at low temperatures. Wang, et al., CN101838616B, describe *Halomonas xianhensis* A-1 CGMCC No 2941 which can degrade various kinds of polyaromatic hydrocarbons.

Contamination of aromatic compounds such as pyrene is a growing worldwide concern since these compounds are recalcitrant to bio-degrade and therefore persist longer in the environment. Moreover, this situation is even worse when the contamination occurs under hypersaline conditions. Existing technologies to remove pyrene including physical and chemical treatments are inefficient, costly and generate toxic byproducts. Consequently, the inventors sought to develop a cheap and safe biological remediation process, especially for pyrene contaminants in a saline environment. Using soil contaminated samples from the Arabian Gulf coastline, halophilic bacteria capable of biodegrading PYR were isolated, characterized and selected for their abilities to degrade pyrene and other PAHs.

In view of the need for an efficient method of degrading PAHs, especially at temperatures above 20° C. and under conditions of salinity exceeding 5 wt % NaCl, it is one object of the present disclosure to identify and isolate halophiles in the genuses *Halomonas* and *Idiomarina* and describe a method and composition for the degradation or detoxification of mixtures containing smaller PAHs such as NAPH, PHEN, ANT, and salicylate (SALC).

BRIEF SUMMARY OF THE INVENTION

In one embodiment, the invention is directed to a method for degrading a polycyclic aromatic compound (PAH) comprising contacting the PAH with one or more bacteria of the genus *Halomonas* or *Idiomarina* or bacteria having 16s ribosomal RNA-encoding DNA sequence that is at least 80% identical to 16s ribosomal RNA-encoding DNA sequence of *Halomonas* or *Idiomarina*, for a time and under conditions that degrade the PAH. Specific strains include *Halomonas shengliensis* 10 PY 2B, *Halomonas smyrnensis* 20 PY 1A, and *Idiomarina piscisalsi* 10 PY 1A and their homologs. Some preferred embodiments involve performing the method using produced water ("PW") contaminated with pyrene or other PAHs.

BRIEF DESCRIPTION OF THE SEVERAL VIEWS OF THE DRAWING(S)

Figure 1D:
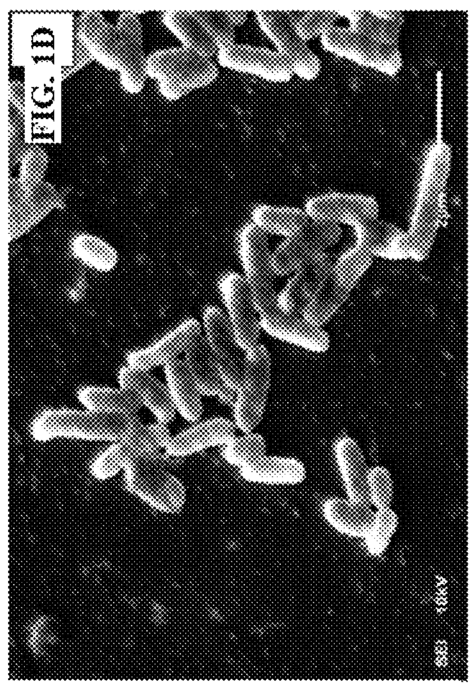
Figure 1A:
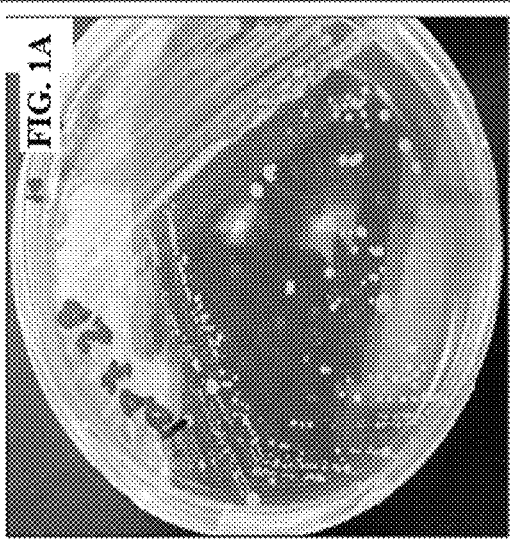

FIG. 1A. Monograph of colony forms of *Halomonas shengliensis* 10PY2B.

FIG. 1B. SEM monograph of colony forms of *Halomonas shengliensis* 10PY2B.

Figure 1C:
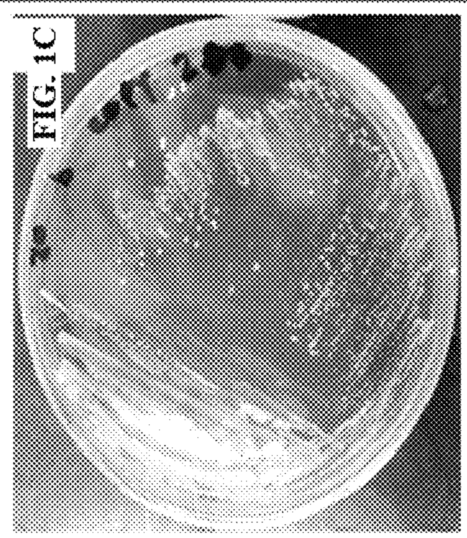

FIG. 1C. Monograph of colony forms of *Halomonas smyrnensis* 20PY1.

FIG. 1D. SEM monograph of colony forms of *Halomonas smyrnensis* 20PY1.

Figure 2:
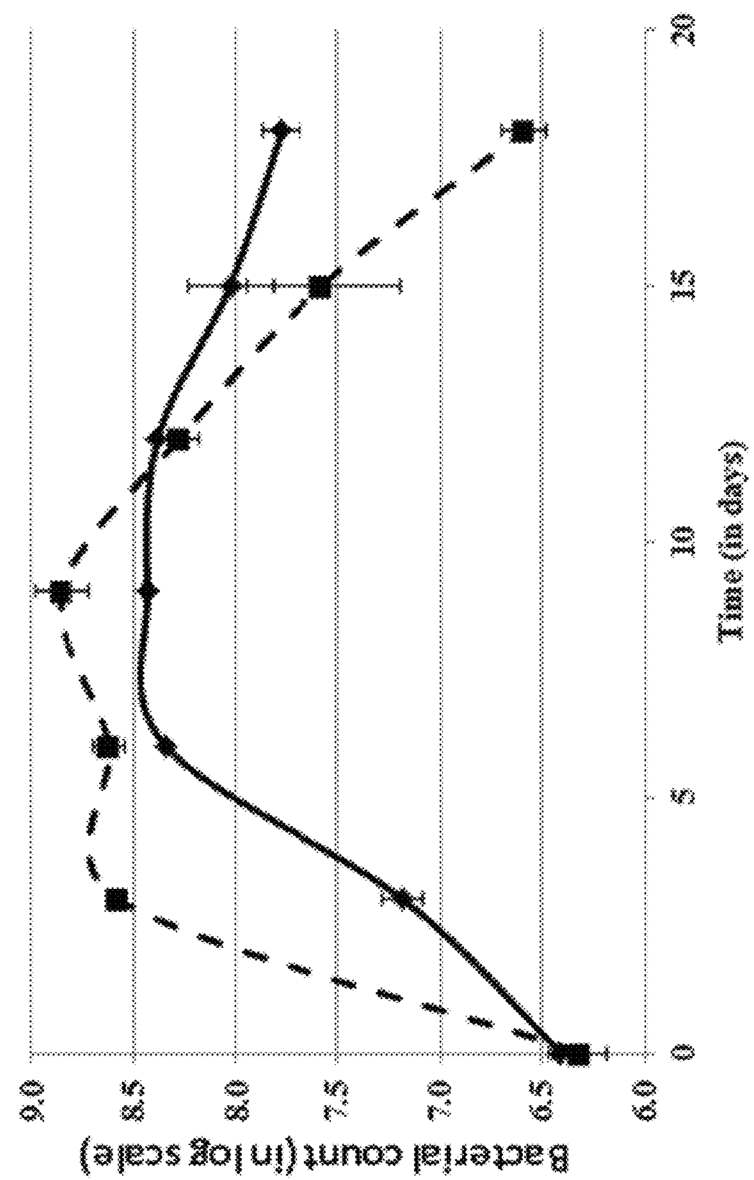

FIG. 2. Growth profile of *Halomonas shengliensis* 10PY2B (solid line with diamonds) and *Halomonas smyrnensis* 20PY1A (dashed line with squares). Cultures were carried out in presence of 50 ppm pyrene.

Figure 3B:
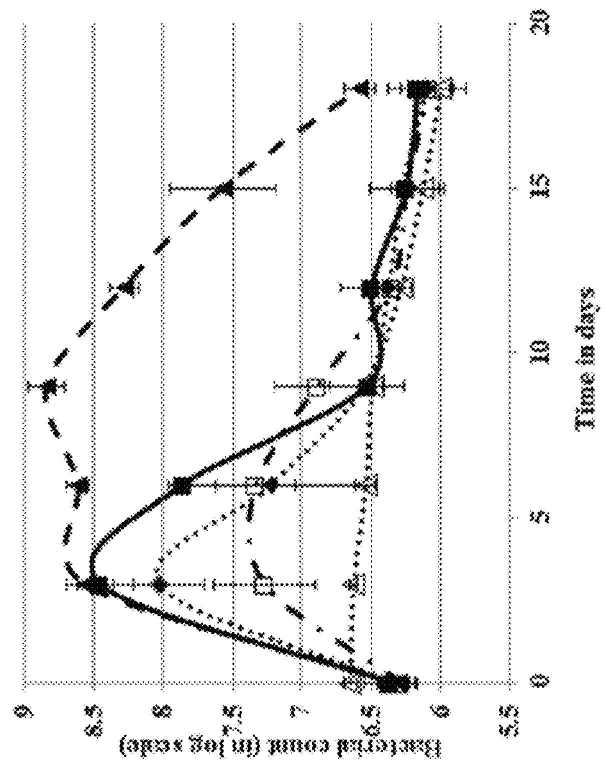
Figure 3A:
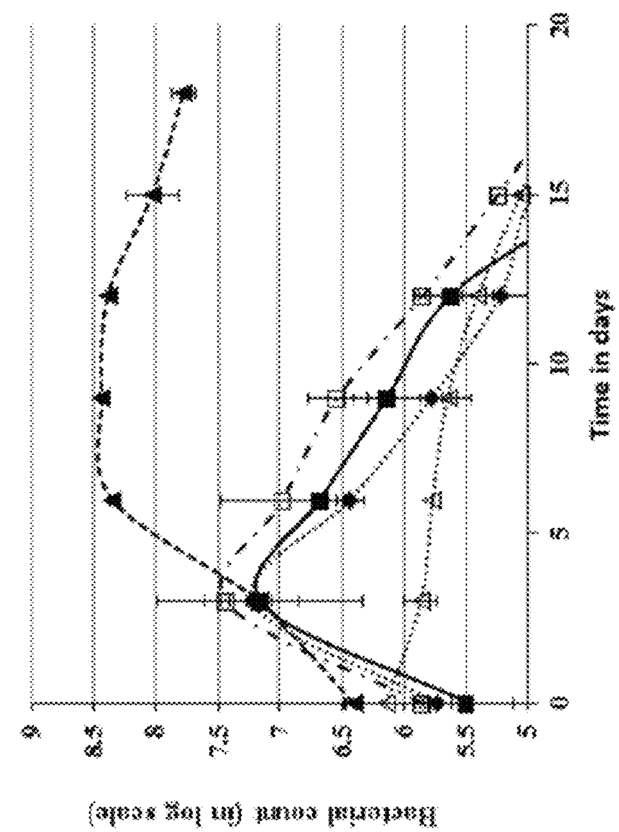

FIG. 3A. Growth profile of *Halomonas shengliensis* at 37° C., pH 7 and 10 wt % NaCl and at various pyrene concentrations. Solid square (1 ppm pyrene), solid diamond (5 ppm pyrene), solid triangle (50 ppm pyrene), unfilled square (100 ppm pyrene) and unfilled triangle (1,000 ppm pyrene).

FIG. 3B. Growth profile of *Halomonas smyrnensis* 20PY1 at 37° C., pH7 and 10 wt % NaCl and at various pyrene concentrations. Solid square (1 ppm pyrene), solid diamond (5 ppm pyrene), solid triangle (50 ppm pyrene), unfilled square (100 ppm pyrene) and unfilled triangle (1,000 ppm pyrene).

Figure 4:
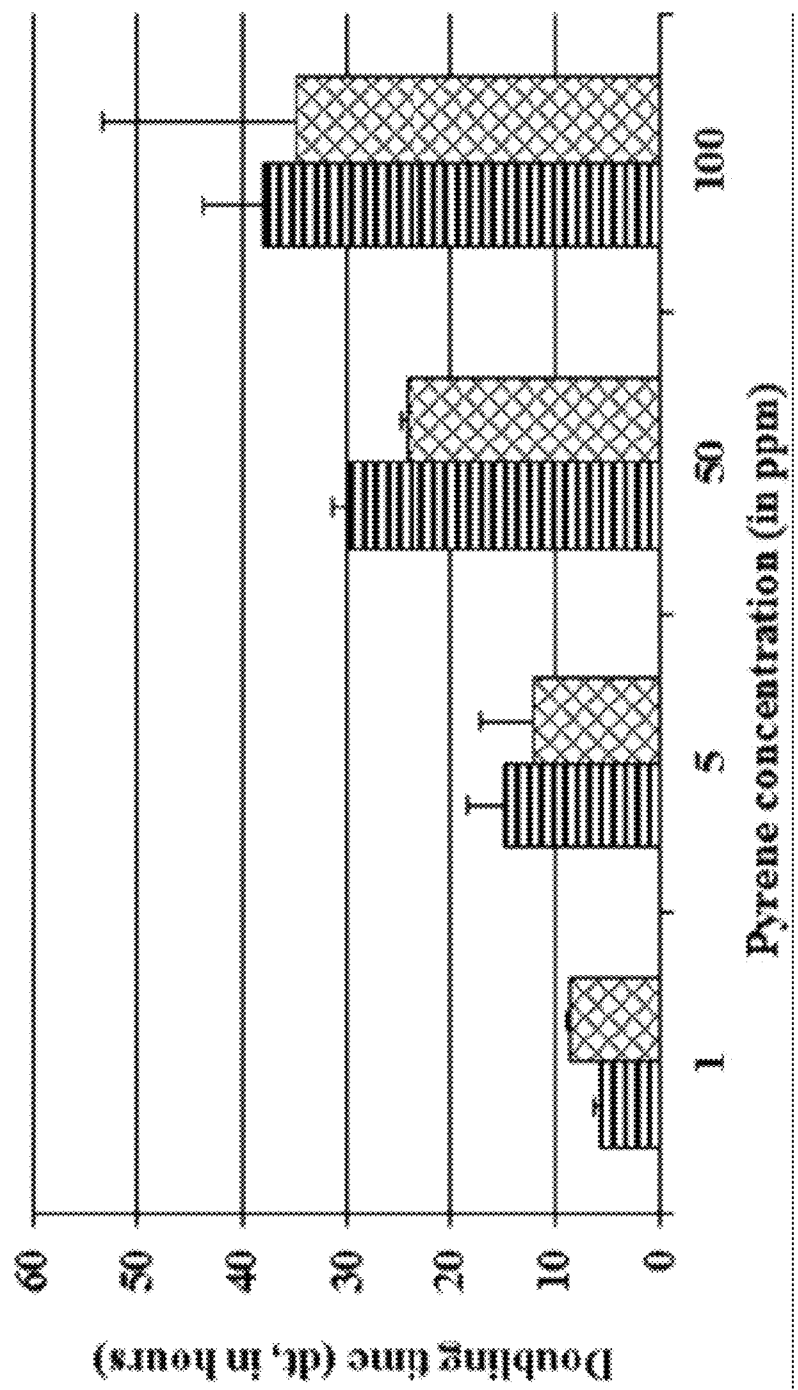

FIG. 4. Doubling times of *Halomonas shengliensis* 10PY2B (stripes) and *Halomonas smyrnensis* 20PY1 (cross-hatch) as a function of pyrene concentration. Experiments were carried out at pH 7, 37° C. and at the salinity conditions described in the Example.

Figure 5:
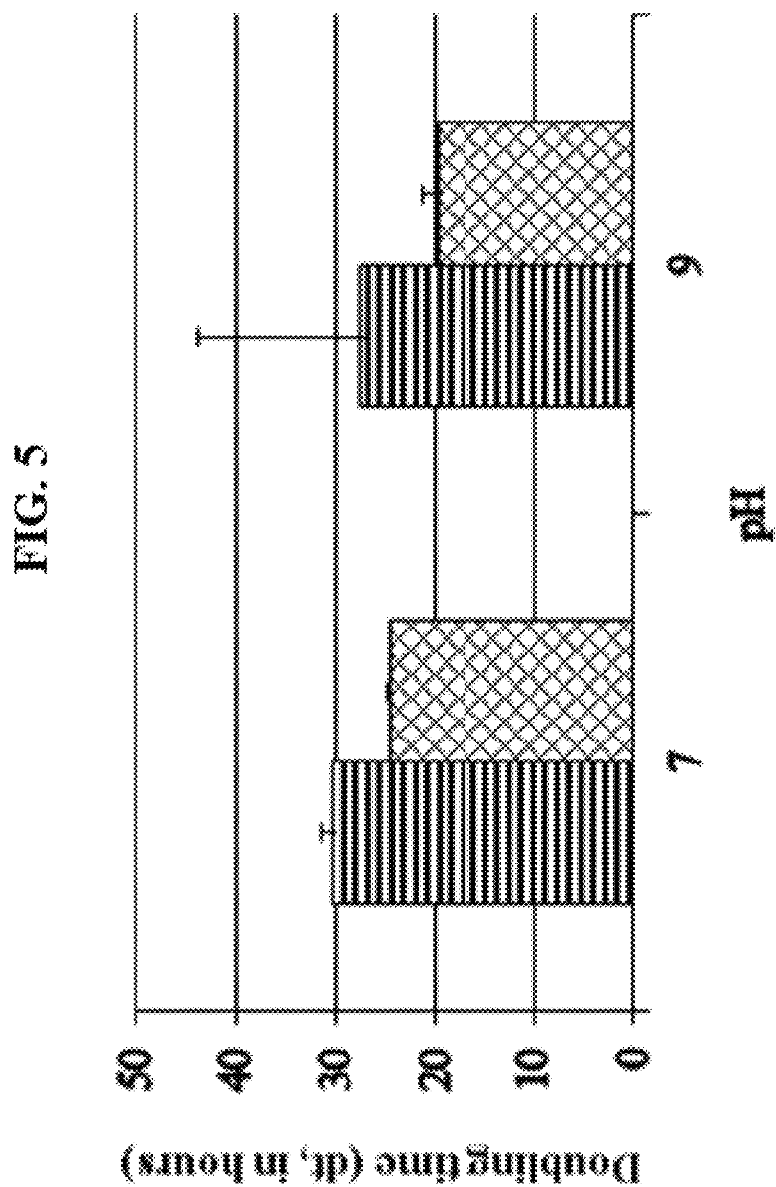

FIG. 5. Doubling times of *Halomonas shengliensis* 10PY2B (stripes) and *Halomonas smyrnensis* 20PY1 (cross-hatch) as a function of pH. Experiments were carried out at pH 7 and pH 9, 37° C. and at the salinity conditions described in the Example.

Figure 6:
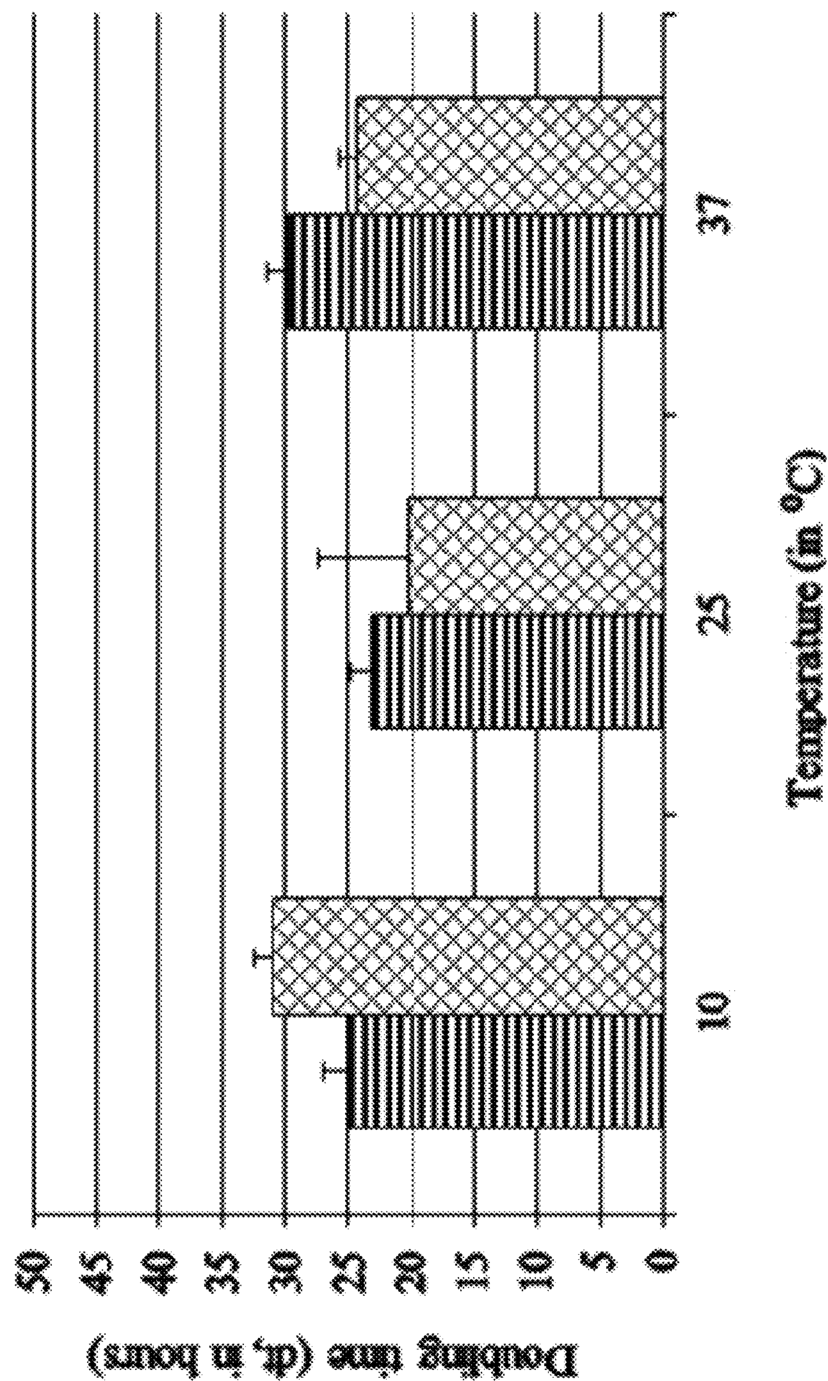

FIG. 6. Doubling times of *Halomonas shengliensis* 10PY2B (stripes) and *Halomonas smyrnensis* 20PY1 (cross-hatch) as a function of temperature. Experiments were carried out at pH 7 and at 10° C., 25° C. and 37° C. and at the salinity conditions described in the Example.

Figure 7:
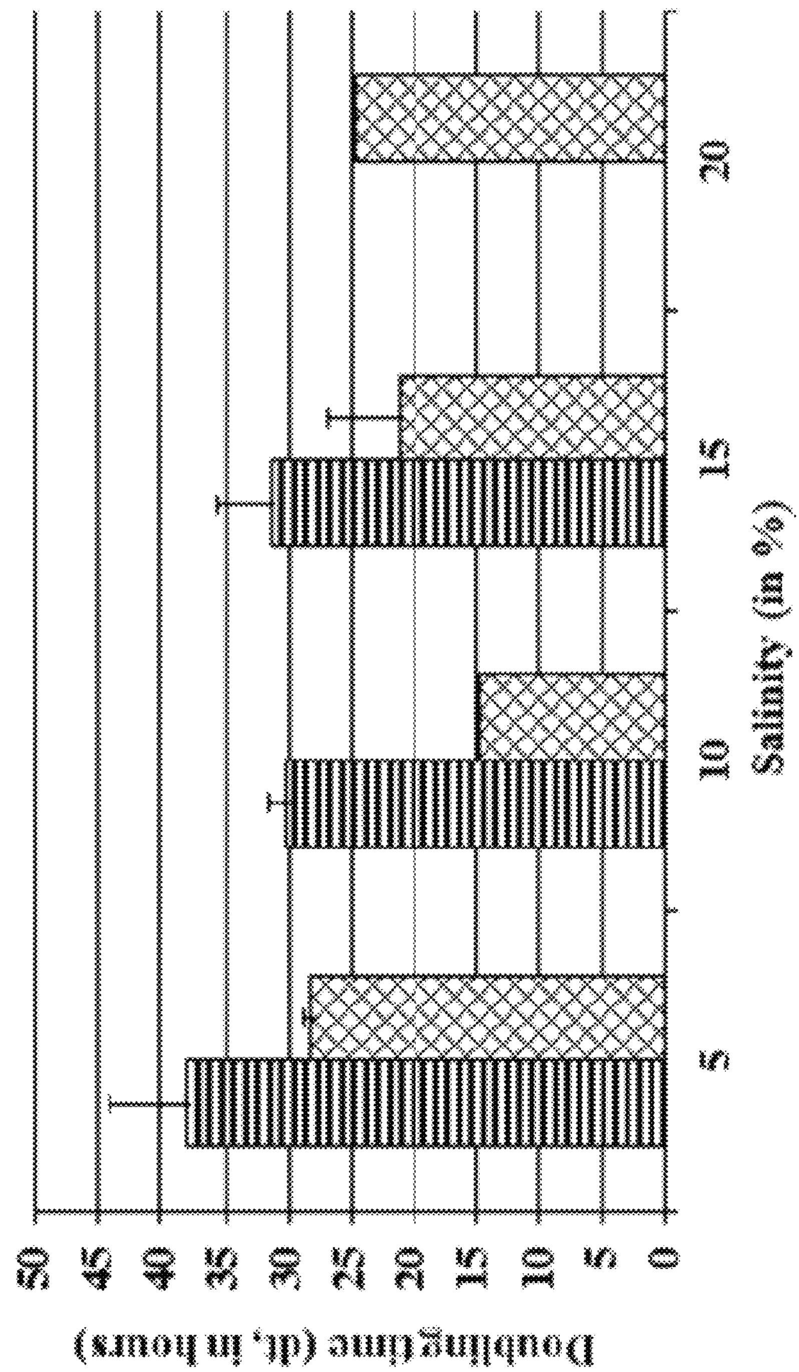

FIG. 7. Doubling times of *Halomonas shengliensis* 10PY2B (stripes) and *Halomonas smyrnensis* 20PY1 (cross-hatch) as a function of salinity. Experiments were carried out at pH 7 and at 37° C. and at 5, 10, 15 and 20 wt % NaCl.

Figure 8:
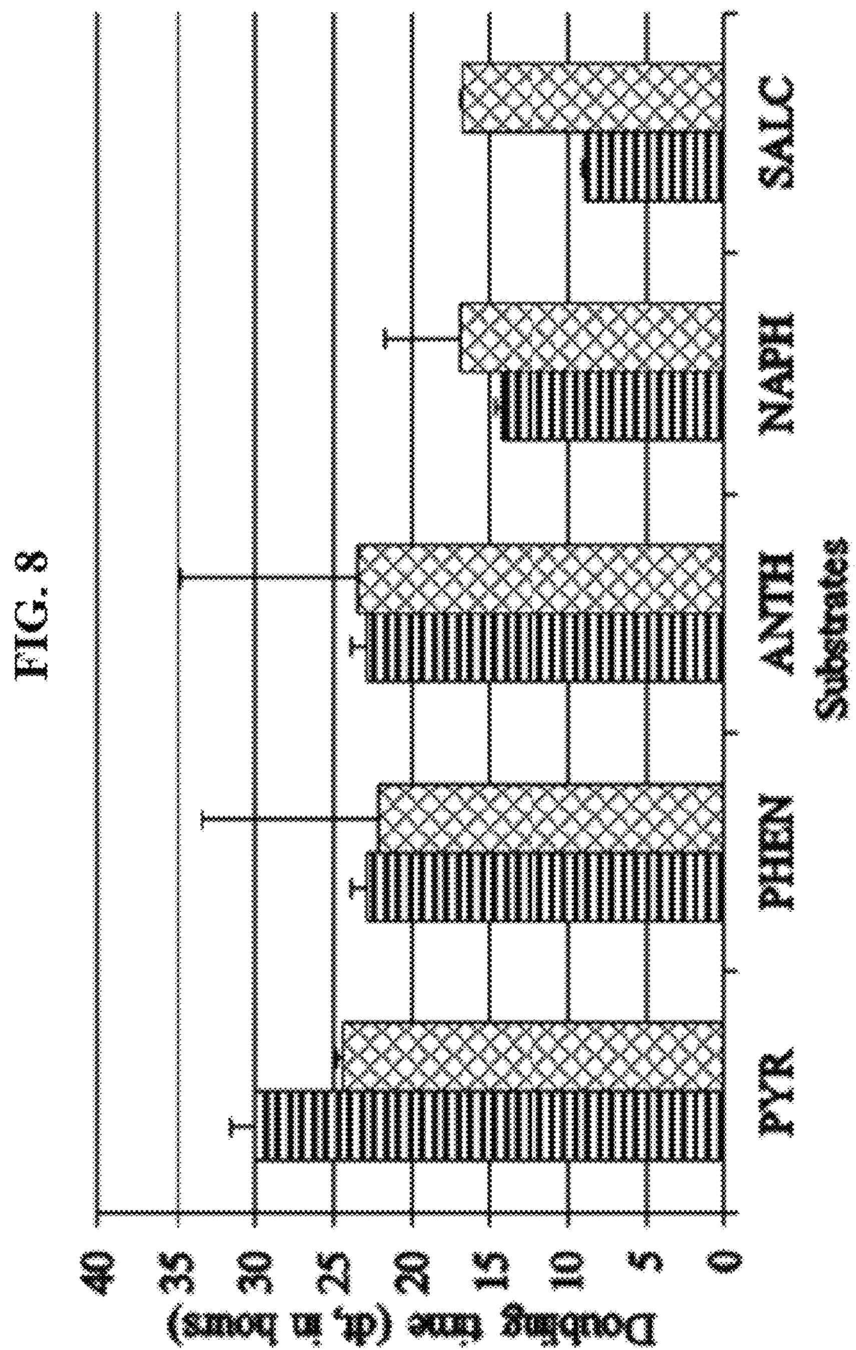

FIG. 8. Doubling times of *Halomonas shengliensis* 10PY2B (stripes) and *Halomonas smyrnensis* 20PY1 (cross-hatch) in presence of various substrates. Experiments were carried out at pH 7 and at 37° C. and at the salinity conditions described in the Example.

Figure 9B:
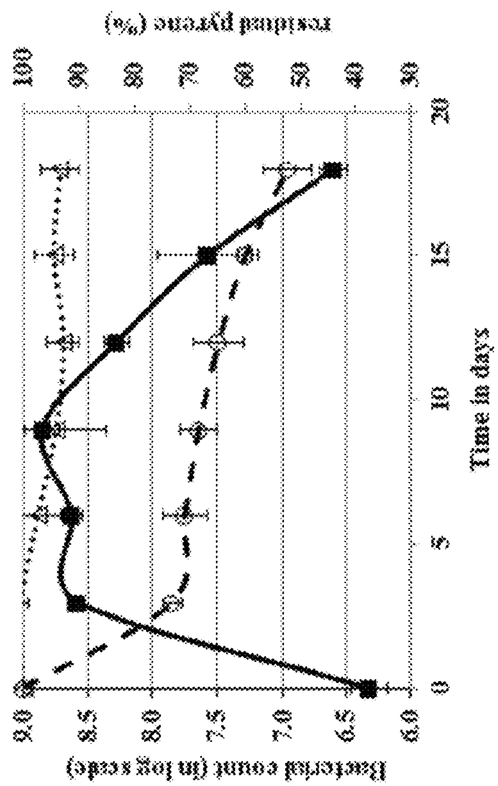
Figure 9A:
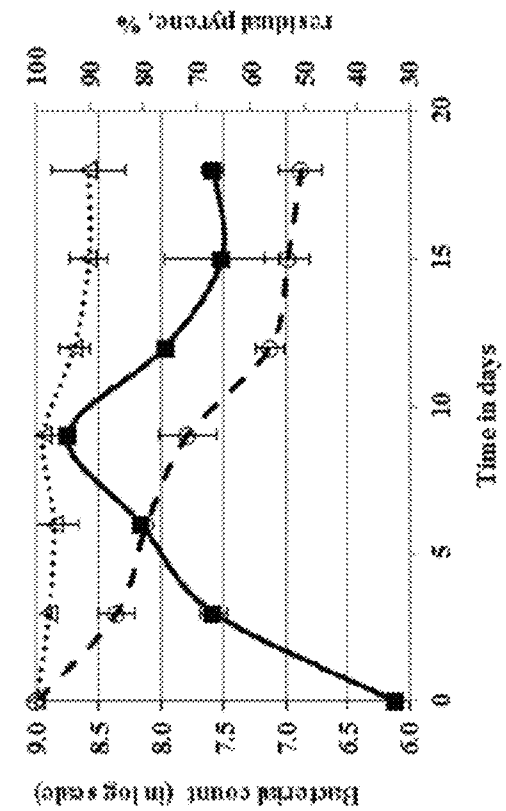

FIG. 9A. Quantification of the remaining pyrene (unfilled circles) in cultures of *Halomonas shengliensis* 10PY2B. Control (no bacteria) denoted by unfilled triangle. Filled squares describe bacterial count.

FIG. 9B. Quantification of the remaining pyrene (unfilled circles) in cultures of *Halomonas smyrnensis* 20PY1. Control (no bacteria) denoted by unfilled triangle. Filled squares describe bacterial count.

Figure 10:
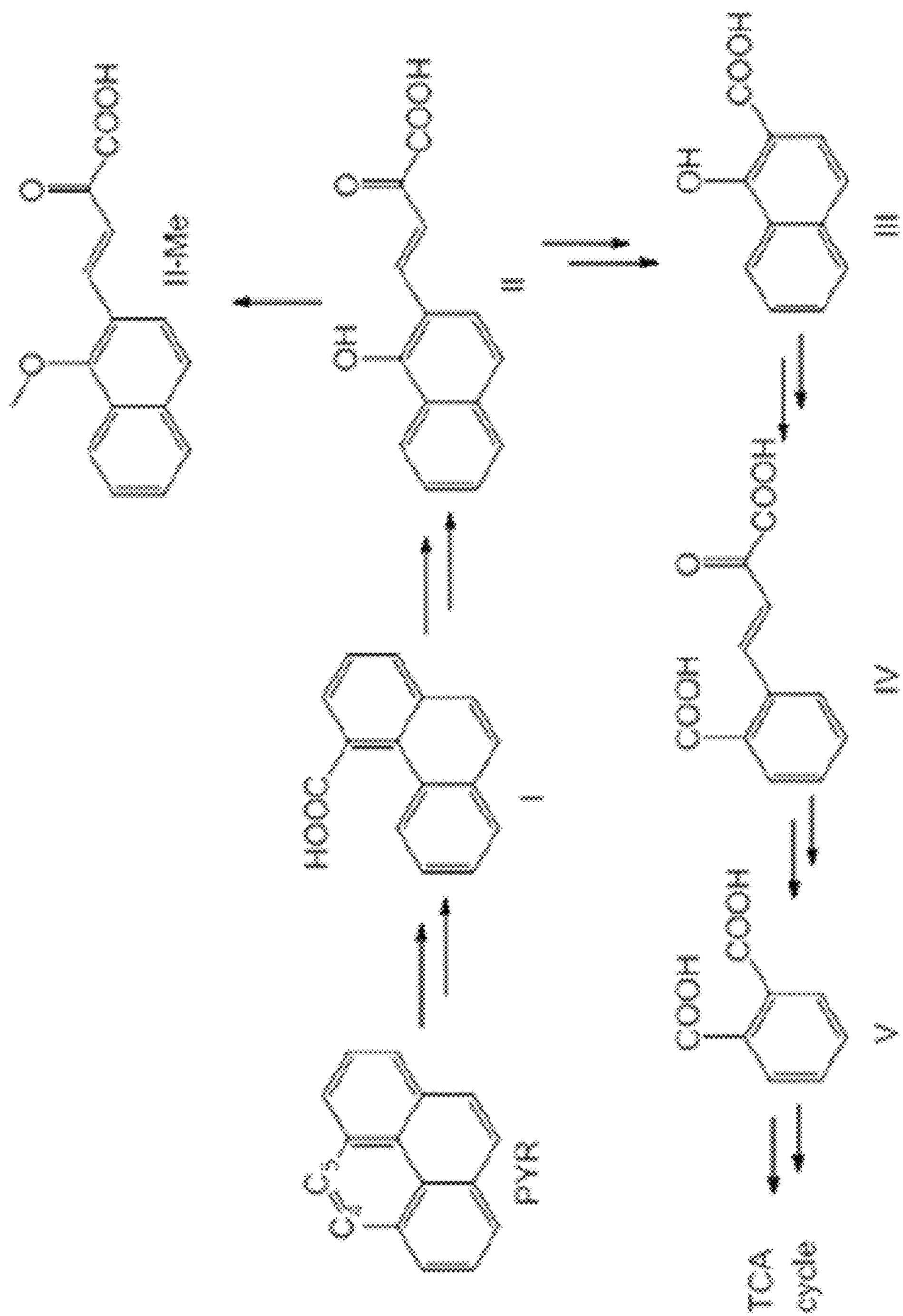

FIG. 10. A proposed metabolic pathway of pyrene biodegradation using of *Halomonas shengliensis* 10PY2B and *Halomonas smyrnensis* 20PY1. I: phenanthrenecarboxylic acid. II: 4-(1-hydroxynaphthalen-2-yl)-2-oxo-but-3-enoic acid. II-Me: 2-(1-methoxynaphthalen-2-yl)-2-oxo-but-3-enoic acid. III: 1-hydroxyl-2-naphthoic acid. IV: 2-carboxycinnamic acid. V: phthalic acid. Metabolites I, II, and V were detected by GC analysis.

FIG. 11. Phenotypic and genetic comparison of microbial strains.

DETAILED DESCRIPTION OF THE INVENTION

Genetic Description of *Halomonas* and *Idiomarina piscisalsi.*

The method of the invention may be practiced with the *Halomonas* or *Idiomarina* strains disclosed herein or with microorganisms that have substantially the same genetic background and phenotypes. Examples of such microorganisms include those that have an rDNA nucleotide sequence that is 80% or more identical, e.g., 80, 81, 82, 83, 84, 85, 86, 87, 88, 89, 90, 91, 92, 93, 94, 95, 96, 97, 98, 99, <100 or 100% identical to a corresponding sequence of *Halomonas* or *Idiomarina* strains disclosed herein.

BLASTN may be used to identify a polynucleotide sequence having at least 70%, 75%, 80%, 85%, 87.5%, 90%, 92.5%, 95%, 97.5%, 98%, 99% sequence identity to a reference polynucleotide. A representative BLASTN setting optimized to find highly similar sequences uses an Expect Threshold of 10 and a Wordsize of 28, max matches in query range of 0, match/mismatch scores of 1/−2, and linear gap cost. Low complexity regions may be filtered or masked. Default settings of a Standard Nucleotide BLAST are described by and incorporated by reference to blast.ncbi.nlm.nih.gov/_Blast.cgi?PROGRAM=blastn&BLAST_PROGRAMS=megaBlast&PAGE_TYPE=BlastSearch&SHOW_DEFAULTS=on&LINK_LOC=blasthome (last accessed Dec. 8, 2017).

Enzymes and other proteins useful for degrading PAHs disclosed herein may have at least 70%, 75%, 80%, 85%, 87.5%, 90%, 92.5%, 95%, 97.5%, 98%, 99%, <100% or 100% sequence identity, or similarity to an enzyme or protein sequence of the *Halomonas* or *Idiomarina* strains disclosed herein.

BLASTP can be used to identify an amino acid sequence having at least 70%, 75%, 80%, 85%, 87.5%, 90%, 92.5%, 95%, 97.5%, 98%, 99%, <100% or 100% sequence identity, or similarity to a reference amino acid using a similarity matrix such as BLOSUM45, BLOSUM62 or BLOSUM80 where BLOSUM45 can be used for closely related sequences, BLOSUM62 for midrange sequences, and BLOSUM80 for more distantly related sequences. Unless otherwise indicated a similarity score will be based on use of BLOSUM62. When BLASTP is used, the percent similarity is based on the BLASTP positives score and the percent sequence identity is based on the BLASTP identities score. BLASTP "Identities" shows the number and fraction of total residues in the high scoring sequence pairs which are identical; and BLASTP "Positives" shows the number and fraction of residues for which the alignment scores have positive values and which are similar to each other. Amino acid sequences having these degrees of identity or similarity or any intermediate degree of identity or similarity to the amino acid sequences disclosed herein are contemplated and encompassed by this disclosure. A representative BLASTP setting that uses an Expect Threshold of 10, a Word Size of 3, BLOSUM 62 as a matrix, and Gap Penalty of 11 (Existence) and 1 (Extension) and a conditional compositional score matrix adjustment. Other default settings for BLASTP are described by and incorporated by reference to the disclosure available at: blast.ncbi.nlm.nih.gov/_Blast.cgi?PROGRAM=blastp&PAGE_TYPE=Blast Search&LINK_LOC=blasthome (last accessed Dec. 8, 2017). Derivatives, analogs or modified versions of any of the polynucleotide or amino acid sequences specifically described herein or in the sequence listing having the above-mentioned ranges of sequence identity or similarly are specifically contemplated including those with 60-100% sequence identity or similarity to a nucleic acid or amino acid sequence disclosed herein.

BLAST may be used to determine the percentage identity or similarity of rDNA of a strain to that of *Halomonas shengliensis* 10PY2B, *Halomonas smyrnensis* 20PY1 and *Idiomarina piscisalsi* 10PY1A described here. Sequences may be compared to full-length rDNA sequences or to partial rDNA sequences given by SEQ ID NOS: 1, 2 and 3. Comparison of microbial variants to *Idiomarina piscisalsi* 10PY1A may similarly be made based on individual gene sequences or on the chromosomal sequences described by GenBank: CP022133.1 (last accessed Dec. 12, 2017), which describes the *Idiomarina piscisalsi* strain 10PY1A chromosome, complete genome. Comparisons to *Halomonas xianhensis* strain A-1 may be made based on the polynucleotide sequence given by SEQ ID NO: 5. In many embodiments, an engineered or variant microbial strain will contain one or more deletions, substitutions, insertions, or transpositions to a polynucleotide of a parental strain such as 1, 2, 3, 4, 5, 6, 7, 8, 9, 10, 15, 20, 25, 50, 100 or more deletions, substitutions, insertions, or transpositions. In other embodiments a variant or engineered strain will contain one or more deletions, substitutions, insertions to one or more polypeptide sequences of a parental strain such as 1, 2, 3, 4, 5, 6, 7, 8, 9, 10, 15, 20, 25, 50, 100 or more deletions, substitutions, insertions.

The invention specifically contemplates new strains of the *Halomonas* or *Idiomarina* bacteria disclosed herein including subcultures, mutational variants, and genetically engineered variants to the strains disclosed herein. Mutation and genetic engineering of bacteria is well known in the art. Mutational and genetically engineered variants will include at least one variation to a gene or genomic sequence of a parental strain. Preferably, such variants will preferably retain or enhance or otherwise modulate the capacity of the parental strain to degrade or metabolize PAHs, such as pyrenes, or increase or decrease its growth at particular temperatures, pH or under altered conditions of salinity or in the presence of toxic metals or other compounds or competing microorganisms. Such variants preferably have at least 70, 80, 90, 95, 96, 97, 98, 99, <100% sequence identity or similarity to partial or whole rDNA sequences or to entire chromosomal sequences of the strains disclosed herein.

Variants, such as epigenetic variants or other types of non-genetic or phenotypic variants, are also contemplated. These may be produced by serial passage and selection of the strains disclosed herein in a medium that selects for growth and viability at a particular temperature, pH, salinity, or in the presence of toxic metals or compounds, or in the presence of competing microorganisms. Such variants will generally exhibit at least one phenotypic variation compared to a parent strain. For example, their growth rate may be 1, 2, 3, 4, 5, 6, 7, 8, 9, 10, 15, 20, 50 or 100% (or any intermediate value) higher under the same culture conditions or they may have the same or higher growth rate than a parent strain when pH, temperature or salinity is varied (increased or decreased) by 1, 5, 10, 25, 50 or 100% (or any intermediate value) of an optimal value for a parent strain. For example, a *Halomonas* or *Idiomarina* variant may exhibit the same or higher growth rate at a pH ±0.25, 0.5, 1, 1.5, 2.0, 2.5 or 3.0 different than the optimal pH for growth or ability of the parental strain to degrade one or more PAHs, may exhibit the same or higher growth rate at a temperature ±1, 2, 3, 4, 5, 6, 7, 8, 9, or 10° C. different than the optimal temperature for growth of the parental strain or for its ability to degrade one or more PAHs, or may exhibit the same or higher growth rate when the salinity is increased or decreased by 1, 2, 3, 4, 5, 6, 7, 8, 9, or 10 wt % compared to the optimal salinity for growth of the parental strain or for its ability to degrade one or more PAHs.

The term "mutant" should be understood as a strain derived from a strain of the invention by means of genetic engineering, radiation, chemical treatment or selection. It is preferred that the mutant is a functionally equivalent mutant, e.g. a mutant that has substantially the same, or improved, properties (ability to degrade PAHs or pyrene) as the parental strain. Such a mutant is a part of the present invention. Especially, the term "mutant" refers to a strain obtained by subjecting a strain of the invention to any conventionally used mutagenization treatment including treatment with a chemical mutagen such as ethane methane sulphonate (EMS) or N-methyl-N'-nitro-N-nitroguanidine (NTG), UV light or to a spontaneously occurring mutant. A mutant may also be a bacteria that has been transformed or transfected with exogenous DNA, such as with a plasmid conferring antibiotic or heavy metal resistance or a plasmid containing genes that degrade PAHs or enhance PAH degradation by a parental strain.

The term "variant" should be understood as a strain which is functionally equivalent to a strain of the invention, e.g. having substantially the same, or improved, properties (e.g., for degrading a PAH such as pyrene). Such variants, which may be identified using appropriate screening techniques, are a part of the present invention. A variant may contain epigenetic alterations or non-genetic modifications that affect its ability to degrade a PAH, its growth rate, or its viability.

In some embodiments *Halomonas* or *Idiomarina* bacterium will be capable of utilizing sucrose, maltose, alpha-lactose, or D-xylose, may be oxidase, catalase or urease positive, and/or may be resistant to antibiotics such as clindamycin, vancomycin, ceftriaxone, cefotaxime sodium, ceftazidime, cefotaxime sodium, ciprofloxacin, gentamicin, streptomycin, ampicillin, clarithromycin, erythromycin, penicillin or tetracycline. In other embodiments, the *Halomonas* or *Idiomarina* will lack one or more of these abilities. In some preferred embodiments the contaminants in PW or other wastes, such as pyrene or other PAHs, will be the primary carbon sources to feed the halophilic bacteria. In other embodiments, alternative carbon sources may be included as needed to facilitate the growth of a halophilic bacterium or increases its capacity to degrade pyrene or other PAHs. Thus, in some embodiments, a strain of *Halomonas* or *Idiomarina* will be used that is capable of growth on one or more carbon sources such as anthracene, phenanthrene, carbazole, naphthalene, or pyrene. In other embodiments, the microorganism may grow on some PAHs as carbon sources, but not on others, for example, it may grow on pyrene, but not grow on one or more of anthracene, phenanthrene, carbazole, or naphthalene. In other embodiments, the microorganism will grow faster or grow to a higher titer on one of anthracene, phenanthrene, carbazole, naphthalene, or pyrene than it does on the other compounds. In some preferred embodiments, a microbial strain of the invention will grow under high salinity (e.g., 10-15 wt % NaCl) and will degrade pyrenes and other PAHs such as anthracene, phenanthrene, naphthalene and salicyclic acid at temperatures ranging from about 30° C. to 40° C.

Attachment.

The microbes of the invention may be unattached (e.g., free in a solution or solid medium) or attached to a carrier, bead, bulking agent, film, or other substrate.

Mixtures.

As disclosed herein, the different strains of halophilic bacteria exhibit optimal abilities to degrade pyrenes or other PAHs under different conditions, for example, they exhibit optimal activity at different salinities. Thus, combinations of two or three of these different microbes may be formulated to facilitate pyrene or PAH degradation under different conditions. In some embodiments, the invention may be practiced in combination with other microbes, including bacteria, fungi, and yeasts, that facilitate degradation of PAHs and other contaminants, especially those that remain active under conditions of high salinity. In some embodiments, microbial mixtures may act directly on contaminants or produce surface-active substances that allow for more efficient microbial biodegradation of hydrocarbons in bioremediation processes. A surfactant or biosurfactant may be used to increase the surface area of hydrophobic water-insoluble substrates such as petroleum contaminants as growth of microbes on hydrocarbons can be limited by available surface area of the water-oil interface. Emulsifiers can break up oil into smaller droplets, effectively increasing the available surface area. Surfactants can also be used to increase the bioavailability of hydrophobic water-insoluble substrates such as PAHs. Surfactants can enhance the availability of bound substrates by desorbing them from surfaces such as soil or sediment or by increasing their apparent solubility. Some biosurfactants have low critical micelle concentrations (CMCs), a property which increases the apparent solubility of hydrocarbons by sequestering hydrophobic molecules into the centers of micelles.

PAH Content.

In some embodiments, the aromatic content in polycyclic hydrocarbon waste such as process water processed according to the invention may range between 0.01 to 100% by weight, or any intermediate value or subrange between 0 and 100. These include 0.1 to 10 wt %, 10 to 50 wt %, and 50-100 wt %. Hydrocarbon waste includes polycyclic aromatic hydrocarbons and these specific wastes disclosed herein. Compositions containing lesser amounts of PAH may also be treated, such as amount less than 100 ppm, less than 50 ppm, less than 10 ppm and 1 ppm or less.

Salinity.

Advantageously, the microorganisms of the invention are capable of degrading a PAH in soil, a solid or semisolid, or liquid material having a high salt content such as at least 5, 10, 15, 20, 25 or 30 wt/wt % NaCl and at high temperatures of 15, 20, 25, 30, 35, 40, 45, 50, 55, 60 or 70° C. or more.

pH.

The method of the invention may be performed at a pH conducive to degradation of a target PAH. Preferably, the method is performed at a pH or above 6.0, preferably 6.5, 7.0, 7.5, 8.0, 8.5, 9.5 or 10, more preferably between 7.0 and 9.0.

Temperature.

According to the present invention, the bioremediation is performed at a temperature suitable for the action of microorganisms between 0° C. to 80° C., preferably at least 20, 25, 30, 35, 40, 45, 50, 55, 60, 65, or 70° C. The temperature may be maintained by heating, spraying and injecting hot water or by other heating means such as by absorption of solar radiation or from solar heated water or other heat conductors. In cold environments, a heat conductor may be inserted into soil so that heat from a heat source can be transferred to soil. Alternatively, the heat conductor inserted in the biopile is electrically energized to heat the biopile. Any material which can transmit heat such as metal and ceramics may be used as a heat conductor. The invention therefore provides a safe, effective and inexpensive means for remediating sludge and soil contaminated with aromatics such as PAHs from environment in such a manner that the aromatics are converted to a growth enhancing humus-like environmentally acceptable product.

Nutrients.

Materials containing nitrogen, phosphorus and essential minerals, trace elements, and vitamins may be used to feed microbes during their degradation of PAHs. One or more ingredients present in conventional *Halomonas* or *Idiomarina* growth or culture media may be added. For example, one or more complex hydrocarbons besides the PAH to be degraded, including crude oil, diesel fuel and lubricating oil may be included or simple hydrocarbons such as octane, decane, hexadecane, methylcyclopentane, methylcyclohexane, heptamethylnonane, benzene, toluene, ethylbenzene, m-, o- and p-xylenes, naphthalene, carbazole, anthracene and phenanthrene, may be used as additional carbon sources. One or more components of a basal medium may be included such as $KH_2PO_4$, $NH_4Cl$, $MgCl_2$ $CaCl_2$, yeast extract or trace-element solution.

In Situ Processing.

Other systems involve holding pools/ponds, effluent catches, or other artificial or natural reservoirs or bodies of water containing PW or other wastes contaminated with pyrene or PAHs or dedicated to bioremediation of PAHs. Landfills and other solid waste dumps or disposal areas may also be mentioned. These may be inoculated or otherwise contacted with a microbe according to the invention under conditions analogous to those described below for a bioreactor. In some embodiments, the microbes may be pumped into contaminated ground water. In some embodiments, air is pumped into a body of contaminated PW or other liquid, or periodic or intermittent agitation may be applied to facilitate contact between microbes and contaminants. In some in situ methods, pellets or particles containing viable halophilic microbes are introduced. These may sediment or embed in contaminated sludge at the bottom of the pool, reservoir or other body of water and release viable halophilic bacteria, or halophilic bacteria and nutrients, over a prolonged period of time, such as over a period of one day, week, one month, three months, or one year or more (or any intermediate time period). Halophilic bacteria may be encapsulated in a polymer or matrix of choice which may be designed to slowly dissolve and release viable halophilic bacteria at different temperatures, pHs, or at different salt concentrations such as any of those described elsewhere herein. A mixture of different polymers containing different bacteria may be applied, for example, separate mixtures for each of the *Halomonas* or *Idiomarina* strains disclosed herein may be prepared and designed to release viable microbes at optimal or preferred pH, saline concentrations, or temperatures. Alternatively, viable halophilic bacteria as disclosed herein may be introduced on lighter materials that float on or become suspended in a contaminated pool, reservoir or body of water to increase the surface area of exposure between the microbes and contaminated water or other material.

Bioreactor.

In some embodiments, the method of the invention is performed in part or in whole in a bioreactor. These may include the so-called "pump and treat" methods in which contaminated groundwater is pumped to the surface, cleaned by passing the groundwater through a bioreactor, and then reinjected into the groundwater. The bioreactor may be one element in a system of mechanical or electronic elements that process and control the flow and exposure of a material containing a PAH to a microorganism of the invention. The method may also be performed in two or more bioreactors which may be arranged sequentially and independent supplied with nutrients that facilitate degradation of PAHs. In other embodiments, the method of the invention may be performed directly in a liquid solution that contains PAHs without a bioreactor by the inoculation of the solution with one or more microorganisms of disclosed herein and/or nutrients.

Material, such as a liquid or flowable material such as produced water ("PW"), contaminated with polycyclic aromatic hydrocarbons (PAHs) may be directed into a bioreactor or system containing one or more bioreactors, and inoculated or otherwise contacted with the microorganisms described herein, so that the PAHs are subsequently degraded. Such system may assay PAH levels and recirculate a contaminated material until a desired low level of a PAH contaminant is attained.

The bioreactor may be configured to maintain a suitable salinity (e.g., 5, 10, 15, 20, 25, 30 wt % NaCl), a suitable pH, such as a pH at or above 7.0, 7.5, 8.0, 8.5, 9.5 or 10, a suitable temperature, such as one at or above 25, 30, 40, 50, 55, or 60° C., as well as adequate levels of oxygen, nutrients, alternative carbon sources, sugars, vitamins, salts, minerals, trace elements, a nutrient medium, antioxidants, carriers, buffers, or other excipients or cofactors conducive to degradation of pyrene or other PAHs.

Batch Processing.

In other batch like systems, the contaminated PW or other material may be held statically, or periodically agitated or mixed, until a desired lower level of PAH contaminant is attainted.

Soil or Biopile.

The method of the invention may be performed in a biopile, soil or other solid or semisolid material by inoculation or incorporation of the microorganisms into a material containing a PAH. The method may be conducted under similar conditions (pH, temperature, nutrient addition, etc.) as described for the method as performed in a bioreactor. Biopiles, also known as biocells, bioheaps, biomounds and compost piles, are used to reduce concentrations of polycyclic aromatic hydrocarbons including petroleum constituents in soils through the use of bioremediation. Biopiles are above ground, engineered systems that use oxygen, generally from air, to stimulate the growth and reproduction of aerobic bacteria which, in turn, degrade the petroleum constituents adsorbed in soil. Biopiles are commonly aerated by forcing air to move through the biopile by injection or extraction through slotted or perforated piping placed throughout the pile. In some embodiments, the invention involves heaping contaminated soils into piles and stimulating microbial activity in the soils through addition of a microbe according to the invention, other hydrocarbon degrading microbes, aeration and/or nutrients and moisture.

Carriers.

The microbes disclosed herein may be introduced in free form or introduced on a carrier. For example, a single or multiple types of halophilic bacterial described herein may be adsorbed on suitable carrier and dispersed in soil while being supported on a carrier. The carrier used includes any known material so far as it can be applied to or incorporated into a contaminated soil or other solid or semisolid material. A carrier may be admixed, adsorbed to, or infused with one or more microbes of the invention, other microbes, nutrients, or PAH-containing material to be remediated or degraded by microbial action. A carrier may act as a growth substrate and facilitate multiplication and spreading of a microorganisms or increase its contact with a PAH in a contaminated material. It may act as a nutrient source, including as a gradual or time-released nutrient source, for the microorganisms thus applied, particularly a nutrient source, which can be gradually released to advantage. Preferably, a carrier will be biodegradable. Further, the carrier is a biodegradable material so that after action of a microorganism of the invention it may be removed leaving the treated material or site in a more natural state. A carrier or bulking agent may be added at a ratio of 1-<100% wt/wt % of the hydrocarbon waste-soil mixture, for example, from 5-50 wt % or from 10-30 wt %, or any intermediate value or subrange. A carrier or bulking agent may comprise, agricultural wastes, tree litter including fronds, leaves, needles, wood chips, bark, grain or maize husks or cobs, bagasse, bark, post peelings, fruit waste, stones, individually or in mixture thereof. These may be ground or granulated to increase surface area and to facilitate mixture into a solid or semisolid material.

A carrier may contain water, for example, it may contain about 0.1% to 99% by weight, 5% to 90% or 10% to 85% by weight of water or another liquid non-toxic to microorganisms used to degrade PAHs. It may contain one or more nutrients for the microorganisms according to the invention. When water content of the carrier is too low, microorganisms do not thrive and struggle to replicate and survive. On the contrary, when the water content of the carrier is too high, the resulting carrier exhibits a deteriorated physical strength that makes itself difficult to handle. The carrier adsorbed microbial blend is tested for its efficacy in liquid medium as well in a biopile.

According one embodiment of the invention, the biopile comprises a layer of soil at the base, a layer of the mixture of the aromatic waste, soil and a bulking agent, a pipe for aeration, drainage and addition of water. The pipe may a perforated polyvinyl chloride (PVC) pipe wrapped with fine cloth, a layer of soil above the mixture and a layer of perforated plastic sheet to cover the biopile and avoid volatile organic compounds (VOCs). The water content within the biopile is maintained by sprinkling the water at the top and sides of the biopile or by using water reservoir or irrigation system (e.g., drip or soaker hoses). The addition of pH adjuster (e.g., to provide an alkaline pH), nutrients and moisture may be combined. The moisture content of the biopile is maintained preferably from 30% to 80% of the water retention capability of the soil-aromatic hydrocarbon waste mixture. When the water content is too low, microorganisms find difficulty in survival. On the contrary, when the water content is too high, it stops aeration. The aeration is maintained by passive diffusion of air using perforated pipes, extraction or injection of air with suitable device or by tilling at every month interval.

Biosensors.

In some embodiments, the microbes of the invention may be employed as biosensors to identify and quantify target compounds such as PAHs or particular PAHs through interaction of the microbes with these compounds. Growth rate may be used as one indicator of the presence of absence of a PAH or, alternatively, genetic markers including quantity of mRNA expression or expression of reporter genes, involved with degradation of a PAH. For example, the microbes disclosed herein may be modified to indicate the presence of a PAH or the expression of a microbial gene used to degrade a PAH. Methods of introducing fluorescent and other reporter genes (GFP, lux, luc) into a microbe and evaluating a change in metabolic status are known in the art, for example, as described by Troegl, et al., Sensors (Basel) 12(2):1544-157 (2012) which is incorporated by reference.

Commercial Use of Invention.

The method of the invention may be used in an industrial, commercial, domestic or other environment for degradation or remediation of PAHs and associated compounds. For example, it can be practiced wherever undesired PAHs are produced or deposited including those produced by the oil or petroleum industry, plastics industry, agriculture, food or drink industry, clothing industry, packaging industry, electronics industry, computer industry, environmental industry, chemical industry, aerospace industry, automotive industry, biotechnology industry, medical industry, healthcare industry, dentistry industry, energy industry, consumer products industry, pharmaceutical industry, mining industry, cleaning industry, forestry industry, fishing industry, leisure industry, recycling industry, cosmetics industry, pulp or paper industry, textile industry, clothing industry, leather or suede or animal hide industry, tobacco industry or steel industry.

Embodiments of the invention include but are not limited to:

1. A method for degrading a polycyclic aromatic compound (PAH) comprising contacting the PAH with one or more bacteria of the genus *Halomonas* or *Idiomarina* or bacteria having 16s ribosomal RNA-encoding DNA sequence that is at least 80% identical to 16s ribosomal RNA-encoding DNA sequence of *Halomonas* or *Idiomarina*, for a time and under conditions that degrade the PAH.

2. The method of embodiment 1, wherein the PAH is naphthalene (NAPH), anthracene (ANT), or phenanthrene (PHEN).

3. The method of embodiment 1, wherein the PAH is pyrene (PYR).

4. The method of embodiment 1, wherein the bacteria are *Halomonas shengliensis* or bacteria having 16s ribosomal RNA-encoding DNA sequence that is at least 80% identical to 16s ribosomal RNA-encoding DNA sequence of *Halomonas shengliensis* strain 10PY2B and that degrades PAH.

5. The method of embodiment 1, wherein the bacteria are *Halomonas shengliensis* or bacteria having 16s ribosomal RNA-encoding DNA sequence that is at least 80% identical to 16s ribosomal RNA-encoding DNA sequence of *Halomonas shengliensis* and wherein said contacting occurs in an aqueous solution having a pH no more than 7 containing at least 5, 10 or 15 wt % NaCl and at a temperature of at least 25° C.

6. The method of embodiment 1, wherein the bacteria are *Halomonas smyrnensis* or bacteria having 16s ribosomal RNA-encoding DNA sequence that is at least 80% identical to 16s ribosomal RNA-encoding DNA sequence of *Halomonas smyrnensis* strain 20PY2A and that degrades PAH.

7. The method of embodiment 1, wherein the bacteria are *Halomonas smyrnensis* or bacteria having 16s ribosomal RNA-encoding DNA sequence that is at least 80% identical to 16s ribosomal RNA-encoding DNA sequence of *Halomonas smyrnensis* and wherein said contacting occurs in an aqueous solution having a pH no more than 7 containing at least 5, 10 or 15 wt % NaCl and at a temperature of at least 25° C.

8. The method of embodiment 1, wherein the bacteria are *Idiomarina piscisalsi* or bacteria having 16s ribosomal RNA-encoding DNA sequence that is at least 80% identical to 16s ribosomal RNA-encoding DNA sequence of *Idiomarina piscisalsi*. strain 10 PY 1A and that degrades PAH.

9. The method of embodiment 1, wherein the bacteria are *Idiomarina piscisalsi* or bacteria having 16s ribosomal RNA-encoding DNA sequence that is at least 80% identical to 16s ribosomal RNA-encoding DNA sequence of *Idiomarina piscisalsi* and wherein said contacting occurs in an aqueous solution having a pH no more than 7 containing at least 5, 10 or 15 wt % NaCl and at a temperature of at least 25° C.

10. The method of embodiment 1, wherein the pyrene is contacted with *Halomonas shengliensis, Halomonas smyrnensis*, or *Idiomarina piscisalsi* in an aqueous solution containing at least 5, 10 or 15 wt % NaCl.

11. The method of embodiment 1, wherein the *Halomonas* or *Idiomarina* are attached to a carrier.

12. The method of embodiment 1, further comprising providing one or more non-PAH carbon sources, oxygen, or other nutrients or growth factors for *Halomonas* or *Idiomarina* during said contacting.

13. The method of embodiment 1, wherein said contacting occurs in solution or in a volatile, aerosol or gaseous mixture.

14. The method of embodiment 1, wherein said contacting occurs in or on a body of water or in ground water or in produced water (‘PW”).

15. The method of embodiment 1, wherein said contacting occurs in soil, sludge or in or on another solid or semisolid material.

16. The method of embodiment 1, wherein said contacting occurs in a biopile.

17. The method of embodiment 1, wherein said contacting occurs in situ at a contaminated site.

18. The method of embodiment 1, wherein said contacting occurs in a bioreactor.

19. *Halomonas shengliensis* or bacteria having 16s ribosomal RNA-encoding DNA sequence that is at least 80% identical to 16s ribosomal RNA-encoding DNA sequence of *Halomonas shengliensis* strain 10PY2B and that degrades PAH;

*Halomonas smyrnensis* or bacteria having 16s ribosomal RNA-encoding DNA sequence that is at least 80% identical to 16s ribosomal RNA-encoding DNA sequence of *Halomonas smyrnensis* strain 20PY2A and that degrades PAH; or

*Idiomarina piscisalsi* or bacteria having 16s ribosomal RNA-encoding DNA sequence that is at least 80% identical to 16s ribosomal RNA-encoding DNA sequence of *Idiomarina piscisalsi*. strain 10PY1A and that degrades PAH.

20. A composition comprising:

a storage or growth medium containing at least 5, 10 or 15 wt % NaCl, at least one PAH, and one or more bacteria selected from the group consisting of:

*Halomonas shengliensis* or bacteria having 16s ribosomal RNA-encoding DNA sequence that is at least 80% identical to 16s ribosomal RNA-encoding DNA sequence of *Halomonas shengliensis* strain 10PY2B and that degrades PAH,

*Halomonas smyrnensis* or bacteria having 16s ribosomal RNA-encoding DNA sequence that is at least 80% identical to 16s ribosomal RNA-encoding DNA sequence of *Halomonas smyrnensis* strain 20PY2A and that degrades PAH, and/or

*Idiomarina piscisalsi* or bacteria having 16s ribosomal RNA-encoding DNA sequence that is at least 80% identical to 16s ribosomal RNA-encoding DNA sequence of *Idiomarina piscisalsi*. strain 10PY1A and that degrades PAH, wherein said bacteria are present at a titer of at least $10^5$, $10^6$, $10^7$, $10^8$, $10^9$, or $10^{10}$ CFU/mL.

21. A kit comprising:

one or more viable bacteria selected from the group consisting of:

*Halomonas shengliensis* or bacteria having 16s ribosomal RNA-encoding DNA sequence that is at least 80% identical to 16s ribosomal RNA-encoding DNA sequence of *Halomonas shengliensis* strain 10PY2B and that degrades PAH,

*Halomonas smyrnensis* or bacteria having 16s ribosomal RNA-encoding DNA sequence that is at least 80% identical to 16s ribosomal RNA-encoding DNA sequence of *Halomonas smyrnensis* strain 20PY2A and that degrades PAH, and/or

*Idiomarina piscisalsi* or bacteria having 16s ribosomal RNA-encoding DNA sequence that is at least 80% identical to 16s ribosomal RNA-encoding DNA sequence of *Idiomarina piscisalsi*. strain 10PY1A and that degrades PAH; and, optionally one or more carriers, beads, bulking agents, buffers, carbon sources, nutrient, dispersants, dispersing apparatus, reaction vessel, packaging materials, or instructions for use in degrading PAH.

EXAMPLE

Two fast-growing halophilic bacteria, *H. shengliensis* and *H. smyrnensis* were evaluated from their ability to efficiently biodegrade PYR in high salinity conditions of 5-30% NaCl. As demonstrated below, these two strains harbored dt values <24 h when grown in the presence of 1-50 ppm PYR. Suitable growth conditions were found to be at 25° C. and at alkaline or neutral pHs. These strains were found to efficiently biodegrade PAHs of lower molecular than PYR and could also be used in bioremediation of PAHs of four rings or less, which are the most common PAHs found in environment contaminated with petroleum products, including in PW.

Chemicals.

PYR, ANT, PHEN, NAPH, SALC, (NH4)2SO4, KH2PO4, $CaCl_2.7H_2O$, $MgSO_4.7H_2O$, $Na_2HPO_4$ and $FeSO_4.7H_2O$ were purchased from Sigma-Aldrich (St. Louis, Mo., USA). Chemicals used in the preparation of Luria-Bertani Broth (LB) medium were purchased from Difco, USA.

Sample Collection, Enrichment and Isolation of the Bacteria Strains.

Samples were collected from a contaminated area from the shoreline of the Arabian Gulf in the industrial city of Jubail, Saudi Arabia. The enrichment culture was initiated with 1.0 g soil samples in 50.0 mL Bushnell Hass (BH) culture medium containing 10, 20 and 25% NaCl (wt/v). The composition of BH medium is as follows: $(NH_4)_2SO_4$ (2.38 g), $NaH_2PO_4$ (1.36 g), $CaCl_2.7H_2O$ (10.69 g), $MgSO_4.7H_2O$ (0.25 g), $Na_2HPO_4$ (1.42 g) and $FeSO_4.7H_2O$ (0.28 mg) per liter, 1.0 mL of a mixture of trace elements, and 0.1% (wt/v) of PYR; this medium is referred to as BH-PYR. The cultures were enriched by incubation at 37° C. and 120 rpm for 2-3 weeks, followed by a transfer in a fresh BH-PYR medium (1/10, v/v), for another 2-3 weeks. After repeating the process for 4-5 times, and when the bacterial growth could be ascertained (based on visual turbidity), the resulted bacteria suspensions, which are the PYR-biodegrading consortia, were isolated and cryo-preserved using glycerol solution. To isolate the individual bacterial species that form the consortia, cultures were streaked in agar solid plate, made of 1% (wt/v) agar in BH-PYR, at appropriate NaCl concentration, and incubated at 37° C. for 7-15 days. Colonies were isolated and streaked again in new plates to ascertain their purity, and these resulting individual colonies were cryo-preserved for further studies.

Scanning Electron Microscopy (SEM) Analysis:

To carry out the SEM, bacteria were immobilized on small microscope cover-slides and were fixed in a solution of formaldehyde (2.5%, v/v) for 12 h, and they were dehydrated by incubating the samples in a series of ethanol-water solutions (ethanol: 30%, 50%, 70%, 80%, 90% and 95%) and then sputter-coated with gold prior to their observation under the SEM (JEOL JSM-6460LV, Japan), as reported elsewhere (Oyehan & Al-Thukair, 2017).

Species Identification (Sequencing of Bacteria).

The identification of bacteria species was carried out by 16S rRNA sequence as previously described (Alexis Nzila, Thukair, Sankara, Chanbasha, & Musa, 2016).

Assessment of the Bacterial Growth in Presence of PYR and Various Hydrocarbons, Effect of pH and Salinity.

Bacteria were pre-cultured in LB-rich media containing 10 and 20% NaCl, and experiments were initiated with about 106 colony forming unit (CFU)/mL in 50 mL BH medium at the appropriate salinity, and supplemented with hydrocarbons at concentration of 1.0 g/L or less (as will be explicitly mentioned). Growth was monitored by bacterial count and is presented in CFU/mL. Concentrations of hydrocarbon in mg/L correspond to those in ppm if hydrocarbons were fully solubilized in the medium. Although at high concentrations of PAHs such as these currently reported, PAHs are not completely dissolved, however, for the sake of comparison with previous reports; concentrations in mg/L and ppm are used interchangeably throughout this disclosure.

In all experiments, non-polar substrates (PYR, PHEN, NAPH and ANT) were dissolved in dimethyl sulfoxide (DMSO), and this DMSO was evaporated before adding the culture medium. SALC was dissolved directly in BH medium. Bacterial growth in presence of PYR was also assessed at various temperatures (10, 25, 37, and 50 o129 C), pH (3, 5, 7, and 9) and salinity (0, 5, 10, 15 and 20% of NaCl [wt/v]).

To quantify the bacterial growth in these various conditions, data from exponential phases of the growth were fitted in the characteristic growth equation $Qt=Q_o e^{kt}$ (Q is bacterium CFU/mL at time t, $Q_0$ is the starting bacterial count in the culture, and k is the growth rate), using Origin software. Thereafter, the doubling time (dt) of bacterial growth was computed as dt=ln(2)/k (in hours), and the lower the dt the higher the bacterial growth.

Quantification and Kinetics of Residual PYR.

The rate of utilization of PYR was assessed by quantifying the remaining PYR in 100 mL bacterial cultures containing 50 ppm PYR for 18 days. Every 3 days, a sample from one flask was collected for quantification. After sonication for 30 minutes, organic compounds were extracted with ethyl acetate (50 mL×2), and the combined organic layers were dried with calcium chloride and then concentrated to dryness under vacuum. Thereafter, the samples were dissolved in chloroform (500 µL) prior to injection into GC for quantification (as it will described in the following section). The concentration of PYR was deduced from a standard curve that was obtained from the GC analysis of the control flaks containing PYR at concentrations of 1, 5, 25, 50, 100 mg/L in the BH medium (without bacteria). Values of quantified PYR were fitted in the classical exponential of equation, $Q_t = Q_o e^{-kt}$, of substrate utilization by microorganisms (Lu, Guo, Zhang, Lu, & Dang, 2014). Thereafter, the degradation rate, k, was computed.

Detection of PYR Metabolites by GC-MS.

Bacteria were grown for 5 days in 1.0 L media containing PYR at 1,000 ppm. Thereafter, the medium was filtered to remove excess PYR prior to extraction with ethyl acetate (100 mL×3). The combined organic layers was dried with calcium chloride then concentrated to dryness under vacuum. The resulting residue was dissolved in 1.0 mL chloroform and divided into two portions. One part was analyzed by GC-MS without further treatment, and the other part was evaporated to dryness then subjected to derivatization with trimethylsilyl (TMS) group. This process, also known as silylation, consisted of mixing the remaining residue with pyridine (40 μL), N,O-bis-trimethylsilyl acetamide (40 μL) and trimethylchlorosilane (20 μL), followed by an incubation at 80° C. for 10 min under nitrogen. The mixture was then diluted with 1.0 mL chloroform prior to its analysis by GC-MS.

The GC-MS analyses were conducted using an Agilent 6890N GC equipped with an HP-1 [30 m, 0.25 mm (i.d.)] column using Helium as the carrier gas attached to 5975B MS, and the following are the analysis conditions: initial temperature of 60° C. held for 2 min followed by an increase to 240° C. at a rate of 10° C./min, a hold time at 240° C. for 20 min, an increase to 300° C. at 10° C./min, and then hold time for 30 min. The MS analysis conditions: inlet temperature of 250° C. and mass range of 15-550 m/z.

The enrichment experiment was carried out in presence of PYR as a sole source 168 of carbon in BH media containing 10, 20 and 25% NaCl. These experiments on average lasted for 2 months and led to the isolation of two consortia, PYR-Cons-10 and PYR-Cons-20, capable to grow in presence of 10 and 20% NaCl, respectively. No growth was observed in media containing 25% NaCl. The second step of the investigation was to isolate individual bacteria that form these consortia. Thus, consortia were streaked on agar solid plates containing the appropriate NaCl concentration (10 or 20% NaCl) in LB rich medium, and the incubated at 37° C. for 3-5 days. Based on the shape and morphology of colonies, one single colony was identified in each consortium: 10PY2B and 20PY2A, from enrichment in media containing 10 and 20% NaCl, respectively. Light and electron microscopy showed that 10PY2B is punctiform, convex having a size of 1×0.6 μm, while 20PY1A colonies were circular, with no elevation (flat) and an entire margin, and with a size of 1.53×0.75 μm. Both strains harbored entire margins, and they were gram negative. FIG. 1 shows the monographs of each strain. To identify the bacterial species of these strains, 16S rRNA genes were sequenced and compared with the available sequences in the National Center of Biotechnology Institute (NCBI) using the Basic Local Alignment Search Tool (BLAST) program for homology. By fixing threshold of 99% homology, 10PY2B was identified as *Halomonas shengliensis*, GI: 970338913, and 20PY2A as *Halomonas smyrnensis*, GI: 97033891.

Growth of the Bacteria in Normal Conditions.

To establish a growth profile for these strains in presence of PYR as a sole source of carbon, analysis was carried out in presence of 50 ppm PYR at 37° C., pH 7, and in their respective salinity (10 and 20% NaCl). The results are summarized in FIG. 2. With initial bacterial count of around $0.5\text{-}1\times10^6$ CFU/mL, cultures grew to a maximum growth of $0.5\text{-}0.8\times10^9$ CFU/mL within just 9 days. The computation of dt shows values of around 30 and 25 hours for *H. shengliensis* 10PY2B and *H. smyrnensis* 20PY1A, respectively. The gamma-proteobacteria halophile of the genus *Halomonas* have been shown to biodegrade mono-aromatic hydrocarbons including phenol, benzoate, salicylate, cinnamic acid and coumaric acid in presence of 1.5-30% NaCl (Garcia, Mellado, Ostos, & Ventosa, 2004; Garcia, Ventosa, & Mellado, 2005). Dastgheib et al. showed that a mixed culture of *Halomonas* and *Marinobacter* bacteria could biodegrade PAHs including NAPH, PHEN, ANT, fluoranthene, fluorine and PYR (Dastgheib, Amoozegar, Khajeh, Shavandi, & Ventosa, 2012). However, the contribution of *Halomonas* bacteria in this biodegradation cannot be established since they were mixed with *Marinobacter*. The bacterium *H. shengliensis* has been demonstrated to biodegrade crude oil (Y. N. Wang, et al., 2007). Most reported microorganisms that biodegrade PYR in high salinity conditions belong to the halophilic archaeas, including *Haloferax, Halobacterium, Halorubrum, Haloarcula*, and *Natrialba* (Bonfa, Grossman, Mellado, & Durrant, 2011; Erdoğmuş, Mutlu, Korcan, Guven, & Konuk, 2013; Fathepure, 2014), though bacterial strains of genera of *Bacillus, Marinobacter, Ochrobactrum, Thalassospira, Oceanicola*, and *Cycloclasticus* have also been described to biodegrade PYR in various conditions of salinity (Arulazhagan & Vasudevan, 2011; Fathepure, 2014; Khemili-Talbi, Kebbouche-Gana, Akmoussi-Toumi, Angar, & Gana, 2015; B. Wang, Lai, Cui, Tan, & Shao, 2008; Yuan, et al., 2009; Zhou, Wang, Huang, & Fang, 2016). The current study clearly shows that bacteria of the genus *Halomonas, H. shengliensis* and *H. smyrnensis*, can efficiently biodegrade PYR at high salinity.

Assessment of Different Concentrations of Pyrene.

As mentioned earlier, HMW PAHs in general, including PYR, are toxic, and the increase in their concentrations in culture media is associated with a decrease, or even inhibition, of growth. Thus, it is important to establish the effect of varying PYR concentration on the growth of these halophilic bacteria. Consequently, growth was measured as a function of PYR concentration (1, 5, 50, 100 and 1000 ppm). As shown in FIG. 3, at 1 and 5 ppm PYR, the two strains showed rapid growth, reaching a maximum growth within three days, and this maximum growth was higher at 1 ppm ($0.8\times10^8\text{-}5\times10^8$ CFU/mL) than that at 5 ppm ($0.4\times10^8\text{-}2\times10^8$ CFU/mL). In media containing 50 ppm of PYR, the strains maximum counts rose to almost 5-10 times higher ($4\times10^8\text{-}9\times10^8$ CFU/mL), however these values were achieved in 6-9 days (compared to three days at 1 ppm). The use of a higher PYR concentration, 100 ppm, was associated with a reduced growth, and at 1000 ppm, none of the tested strains grew (FIG. 3). These observations were supported by dt values, showing that as PYR concentration increases, the magnitude of dt increases, 5-10, 12-16, 20-30, 32-38 h at 1, 5, 50, 100 ppm, respectively (FIG. 4).

The most efficient (or fast growing) PAH-, including PYR, biodegrading microorganisms reported so far have a dt value of around 24 h (Heitkamp, Franklin, & Cerniglia, 1988; Khan, Kim, Paine, & Cerniglia, 2002). A careful observation of these data shows that concentrations of PAHs used in these experiments are generally less than 100 ppm. For instance, the non-halophile *Mycobacterium vanbaalenii* has been reported as one of the most efficient PYR-biodegrading microorganisms since it can reach maximum a growth (as measured optic density) within 1 day (Heitkamp, et al., 1988). However, this high growth rate was achieved using low PYR concentration of around 0.5 ppm (Heitkamp, et al., 1988; Khan, et al., 2002). In the present disclosure, with the use of PAH concentrations that are 2-10 times higher (1-5 ppm), maximum growth was achieved within three days, 232 corresponding to dt values of less than 24 h. Thus, the efficiency of PYR biodegradation by the present halophilic microorganisms is similar to that of the most efficient non-halophilic strain *Mycobacterium vanbaalenii* in PYR degradation. The currently disclosed strains can grow in presence of high salinity. These data also show that PYR concentrations as high as 1000 ppm inhibits the growth of these halophile growth. It is interesting to note that in general non-halophilic microorganisms still grow at 1000 ppm of PAHs in general and PYR in particular (Hiroshi Habe, et al., 2004; Alexis Nzila, Thukair, et al., 2016).

Variation of pH and Temperature.

To establish the best conditions of bacterial growth, the ability of *H. shengliensis* 10PY2B and *H. smyrnensis* 20PY1A to utilize PYR was assessed at pH 3, 5, 7 and 9. The two strains grew at pH 7 and 9 with maximum growth falling between $10^8$-$10^9$ CFU/mL, which was attained within 6-9 days. However, in acidic media of pH 3 and 5, no growth was observed. The computation of dt showed values between 20 and 30 hours at pH 7 and 9 (FIG. 5). Interestingly, a slight decrease in dt at pH 9 (FIG. 5) was observed for the two strains, an indication that alkaline conditions are more appropriate for the growth of these two *Halomonas* strains. Most of the studies on biodegradation of pollutants, including PAHs, have been carried out in neutral pH (Margesin & Schinner, 2001). Sorokin et al. (2012) reported the biodegradation of one-ring-containing aromatic compounds such as phenol, benzene, salicylate, among others in alkaline media (pH 8-10) by haloalkaliphilic bacteria of the group of *Arthrobacter, Bacillus, Rodococus, Marinobacter*, and *Halomonos*, among others (Sorokin, Janssen, & Muyzer, 2012). Bacteria of the genera *Rhodococcus, Alcalingenes, Acinetobacteria, Dietzia, Pseudomonas* are reported to biodegrade the PAHs PHEN, ANT, fluorine and fluoranthene at pH 8-10; PYR biodegradation by *Rhodococcus* and *Mycobacterium* at pH 9 was also reported (Sorokin, et al., 2012). A recent study showed that 265 the halophilic *Thalassospira* sp. strain can utilize PYR at alkaline pH (Zhou, et al., 2016). However, these experiments were carried out in moderate level of salinity (<5% NaCl). In the current study, PYR biodegradation was carried out in high salinity (10 and 20% NaCl), a clear indication that the isolated strains, *Halomonas shengliensis* (10PY2B), and *Halomonas smyrnensis* (20PY2B) can be used in biodegradation in condition of hyper-salinity and alkalinity.

The effect of temperature on the growth of the two bacterial strains was also evaluated at 10, 25, 37 and 50° C. The two strains exhibited similar growth profiles at 10, 25 and 37° C., with maximum count between 0.5-0.8×$10^8$ CFU/mL, which was achieved within 6-9 days. Interestingly, the computation of dt showed the two strains grew better at 25° C., with dt values falling between 20 and 24 h, while these values increased to 25-30 h at 10 and 37° C. (FIG. 6). Thus, overall, these strains are more efficient in biodegrading PYR at moderate temperature (25 o278 C), and this is in line with many reports on the biodegradation of PAHs in general and PYR in particular, showing that most of the efficient PAHs-biodegrading bacteria are mesophilic (20-45° C.) (Fathepure, 2014; Martins & Peixoto, 2012; Sorokin, et al., 2012). None of the strains grew at 50° C., indicating that these bacteria are not thermophiles. The biodegradation of PYR and other PAHs by thermophilic bacteria (temperature range of 55-70° C.) has been reported, belonging to various genera including *Geobacilli, Bacilus* and *Thermus* (Feitkenhauer & Markl, 2003; Feitkenhauer, Muller, & Markl, 2003; Viamajala, Peyton, Richards, & Petersen, 2007; Zeinali, Vossoughi, & Ardestani, 2008a, 2008b). The dt values of the two strains described in the present disclosure were almost similar at 10 and 37° C., an indication that these bacteria are psychrotolerant (can grow at low temperature), and that they show a wide temperature range at which PYR can be biodegraded.

Salinity.

The strains 10PY2B (*H. shengliensis*) and 20PY1A (*H. smyrnensis*) were isolated in presence of 10 and 20% NaCl, respectively. The ability of these strains to utilize PYR in various conditions of salinity was investigated. Thus, the growth profiles of the two strains were assessed at 0, 5, 10, 15 and 20% NaCl. The data are summarized as dt values in FIG. 7. In absence of salinity, none of the tested strains grew. At 10% NaCl, *H. shengliensis* had a dt value around 30 h; at 15% NaCl, the growth of this strain was similar (dt around 32 h). However, no growth was observed at 20% NaCl. At lower salinity (5% NaCl), the strain could still grow, but with a higher dt compared 297 to the growth at 10% (140 versus 30 h); FIG. 7. At 5%, the dt was higher (around 40 h), an indication that this strain utilize PYR less efficiently at salinity lower than 10% (the salinity at which it was isolated). In relation with *H. smyrnensis* (which was isolated at 20% NaCl), the highest growth was observed at 10% NaCl, with a dt of 13 h, followed at 15% (dt of 20 h); a dt value of 22 h was associated with 20% NaCl. The highest values of dt (27 h) was observed with low salinity of 5% NaCl. Thus, salinity range of 5-15% and 5-20% are appropriate for *H. shengliensis* and *H. smyrnensis*, respectively. Biodegradation date of petroleum products show that most halophilic microorganisms biodegrade PAHs (including PYR) at salinity range of 1-15%, and generally no biodegradation is observed in absence of salinity (Fathepure, 2014). These observations are in line with the characteristics of *H. shengliensis*. Microorganisms that were efficient in biodegrading PAHs at high salinity (20%) generally do not do so at low salinity. The exception was reported with *Actinopolyspora* sp., which could biodegrade the three-ring-containing PAH fluorine within a range of 5-20% NaCl (Al-Mueini, Al-Dalali, Al-Amri, & Patzelt, 2007), the same range as the strain *H. smyrnensis* does. This review also points out that halophilic microorganisms that biodegrade PAHs do not growth in absence of salinity, yet growth can be observe in some microorganisms able to biodegrading mono-aromatic and aliphatic hydrocarbons (Fathepure, 2014).

Utilization of Other Aromatic Substrates.

In a natural environment, aromatic petroleum products are found as mixtures of mono- and poly-cyclic aromatic hydrocarbons. A microorganism that can biodegrade a given PAH may also be capable of utilizing a PAH of lower molecular weight (A. Nzila, 2013). Thus, the ability of the isolated two strains to biodegrade aromatic compounds of lower molecular weight was investigated, and these included the one-ring SALC, the two-ring NAPH, and the three-ring PHEN and ANT. The results are summarized in FIG. 8. The data showed that dt values of the two tested strains increase as the number of rings increases; the ranges of dt were 9-16, 14-17, 18.5-22, and 21.5-24 h, for SALC, NAPH, PHEN and ANT, respectively. In comparison, the use of PYR was associated with higher dt range of 24-30 h. Thus, these strains can biodegrade not only PYR, but also monocyclic aromatic and PAHs of lower molecular weights, as it has been reported with many other bacteria strains (Cao, Nagarajan, & Loh, 2009; A. Nzila, 2013; Seo, et al., 2009).

Assessment of Kinetics 329 of PYR Utilization.

The kinetics of utilization of PYR was also assessed for the two strains, by quantifying the remaining PYR in the culture, every three days, using GC. As FIG. 9 shows, starting with a concentration of 50 ppm, the amount of PYR decreased by 25-40% within 6-9 days in the two tested strains, and this period corresponds to the maximum bacterial count; FIG. 10. Incubation for 18 days resulted in biodegradation of 50% or more of PYR, while in the control, the remaining PYR was more than 90%. The computation of the degradation rate, k, showed that the *H. smyrnensis* is more efficient in biodegrading PYR (k=0.05 day-1) than *H. shengliensis* (k=0.048 $day^{-1}$). Reported studies on the biodegradation of PYR in saline conditions have shown similar results. For instance, using media containing 200 ppm PYR and 5% salinity, halophilic *Thalassospira* sp. biodegraded around 40% of PYR within 25 days (Zhou, et al., 2016). Similar results have been reported on non-halophilic bacteria such as *Caulobacter* sp. (Al-Thukair & Malik, 2016), *Mycobacterium* sp. (H. Habe, et al., 2004; Vila, et al., 2001; S. Wang, et al., 2012), *Pseudomonas* sp. (Ma, Xu, & Jia, 2013), *Leclercia decarboxylata* (Sarma, Duraja, Deshpande, & Lal, 2010), *Diaphorobacter* sp., *Pseudoxanthomonas* sp. (Klankeo, Nopcharoenkul, & Pinyakong, 2009) and *Ochrobactreum* sp. (Arulazhagan & Vasudevan, 2011).

Identification of Pyrene Metabolites.

The mass spectra of PYR metabolites using *Halomonas shengliensis* were analyzed. The GC-MS analysis showed a metabolite with retention time of 22.62 min with a molecular ion ($M^+$) at m/z 328 and fragment ions at 313 ($M^+$-CH3), 297 ($M^+$-$OCH_3$), 145 $(COCOOTMS)^+$, 117 $(COOTMS)^+$, and 73 $(TMS)^+$. This metabolite was identified as the TMS derivative of4-(1-methoxynaphthalen-2-yl)-2-oxo but-3-enoic acid (II-Me). This metabolite was previously reported in pyrene degradation using *Thalassospira* sp. strain TSL5-1 (Zhou, et al., 2016). Another peak that appeared at 41.24 min had an $M^+$ at m/z 386 and fragment ions at 371 ($M^+$-CH3), 313 ($M^+$-TMS), 297 ($M^+$-OTMS), 147 $[(CH_3)_3Si_2]H$, 145 $(COCOOTMS)^+$, 117 $(COOTMS)^+$, and 73 $(TMS)^+$ These fragments are consistent with the diTMS derivative of 4-(1-hydroxynaphthalen-2-yl)-2-oxo-but-3-enoic acid (II). A metabolite with retention time 13.20 min that had $M^+$ at m/z 294 and fragmentation ions at m/z 221 ($M^+$-TMS), 205 ($M^+$-OTMS), 177 ($M^+$-COOTMS), 147, 117 $(COOTMS)^+$, 73 $(TMS)^+$ was identified as the TMS derivative of 4-phenanthrenecarboxylic acid (I). Most of these fragments (221, 205, 177, and 59) were previously observed for the methyl ester of 4-phenanthrenecarboxylic acid (H. Habe, et al., 2004; Zhou, et al., 2016), which produces similar fragments to the TMS derivative of the corresponding acid. These two identified metabolites supports that the oxidation 360 then cleavage of PYR takes place at C4 and C5, as shown in FIG. 10. Another metabolite was observed at retention time 20.03 min that has a base peak at m/z 149 and other fragment ions at 121, 104, 93, 76, 57, and 41. These fragments are consistent with a phthalic acid ester and was confirmed upon comparison with National Institute of Standards and Technology. The fragment at m/z 149 is a characteristic peak for phthalate esters (F. Wang, et al., 2017). The GC366 MS analyses of the PYR metabolites using *Halomonas smyrnensis* indicated the presence of the three metabolites identified for *H. shengliensis*. Based on the identified PYR metabolites by the *H. shengliensis* and *H. smyrnensis*, a tentative metabolic pathway was proposed as shown in FIG. 10. Similar PYR metabolic pathways that includes metabolites I-V in FIG. 10 have been previously reported. For example metabolites I and V in degradation using *Mycobacterium vanbaalenii* PYR1 (Kim, Freeman, Moody, Engesser, & Cerniglia, 2005), *Mycobacterium* sp. Strain KMS (Liang, et al., 2006), and *Bacillus megaterium* YB3 (Meena, Sharma, Gupta, Karmakar, & Aggarwal, 2016), metabolites I, III, and V in degradation using *Pseudomonas stutzeri* CECT 930 (Moscoso, Deive, Longo, & Sanroman, 2015), metabolites I-V in PYR degradation using *Thalassospira* sp. strain TSL5-1 (Zhou, et al., 2016).

As shown herein, halophilic bacteria including strains 10PY2B and 20PY1B were isolated by enrichment culture under high saline conditions. 16s rRNA analyses identified 10PY2B as *Halomonas shengliensis* and 20PY2A as *Halomonas smyrnensis*. These strains were found to have doubling times of less than 24 h when pyrene was used at concentrations <50 ppm, making them as fast growing pyrene-biodegrading bacteria as reference strain *Mycobacterium vabaalenii*. They were more active at neutral to alkaline conditions, and at 25° C., and biodegraded more efficiency aromatic compounds of small molecular weight than pyrene (salicylate, naphthalene, phenanthrene and anthracene). Within 18 days, the strains biodegraded 50% of 50 ppm pyrene, and the use of Gas chromatography/mass spectroscopy led to the identification of the metabolites 4-phenanthrenecarboxylic acid, 4-(1-hydroxynaphthalen-2-yl)-2-oxo but-3-enoic acid, and phthalic acid, consistent with pyrene biodegradation.

Halophile bacteria were isolated from contaminated areas and their ability to grow in various conditions of temperature (10, 25, 37 and 50)° C., pH (3, 5, 7 and 9), salinity (0, 5, 10, 15, 20)% w/v and initial pyrene concentration (1, 5, 50, 100, 1000) mg/l was evaluated. The ability of these bacteria to grow in presence of other aromatic pollutants such as salicylic acid (one ring), naphthalene (2 rings), p and anthracene (3 rings) was investigated also. Two bacteria stains in 10% NaCl, *Idiomarina* sp. 10PY1A and *Halomonas shengliensis* 10PY2B, and one strain in 20% NaCl, *Halomonas smyrnensis* 20PY1A were isolated. These three strains could efficiently grow at alkaline conditions but not at acidic conditions of pH 3 and pH 5. The doubling time of *Idiomarina* sp. 10PY1A, *Halomonas shengliensis* 10PY2B and *Halomonas smyrnensis* 20PY1A at pH 7 was 26 hours, 30 hours and 24 hours, respectively, while the doubling time at pH 9 was 25 hours, 41 hours and 20 hours, respectively. Furthermore, no growth for all isolated strains was observed at 50° C., and the optimum growth for all isolated strains was observed at 25-37° C. Moreover, all isolates grew in all tested salinity except salinity 0%. The optimum salinity for *Idiomarina* sp. 10PY1A, *Halomonas shengliensis* 10PY2B and *Halomonas smyrnensis* 20PY1A was 5%, 10%, and 15%, respectively. The results also show that increase in pyrene concentration was associated with inhibition of growth of 3 strains. On the other hand, during the test of several aromatic compounds as a sole carbon source, the growth rate of all strains correlated negatively with the number of rings of the tested aromatic compounds. The fastest degradation rate was observed in by *Halomonas smyrnensis* 20PY1A at 37° C. and pH 7.

Terminology

Terminology used herein is for the purpose of describing particular embodiments only and is not intended to be limiting of the invention.

The headings (such as "Background" and "Summary") and sub-headings used herein are intended only for general organization of topics within the present invention, and are not intended to limit the disclosure of the present invention or any aspect thereof. In particular, subject matter disclosed in the "Background" may include novel technology and may not constitute a recitation of prior art. Subject matter disclosed in the "Summary" is not an exhaustive or complete disclosure of the entire scope of the technology or any embodiments thereof. Classification or discussion of a material within a section of this specification as having a particular utility is made for convenience, and no inference should be drawn that the material must necessarily or solely function in accordance with its classification herein when it is used in any given composition.

As used herein, the singular forms "a", "an" and "the" are intended to include the plural forms as well, unless the context clearly indicates otherwise.

It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof.

As used herein, the term "and/or" includes any and all combinations of one or more of the associated listed items and may be abbreviated as "/".

Links are disabled by deletion of http: or by insertion of a space or underlined space before www. In some instances, the text available via the link on the "last accessed" date may be incorporated by reference.

As used herein in the specification and claims, including as used in the examples and unless otherwise expressly specified, all numbers may be read as if prefaced by the word "substantially", "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), +/−15% of the stated value (or range of values), +/−20% of the stated value (or range of values), etc. Any numerical range recited herein is intended to include all subranges subsumed therein.

Disclosure of values and ranges of values for specific parameters (such as temperatures, molecular weights, weight percentages, etc.) are not exclusive of other values and ranges of values useful herein. It is envisioned that two or more specific exemplified values for a given parameter may define endpoints for a range of values that may be claimed for the parameter. For example, if Parameter X is exemplified herein to have value A and also exemplified to have value Z, it is envisioned that parameter X may have a range of values from about A to about Z. Similarly, it is envisioned that disclosure of two or more ranges of values for a parameter (whether such ranges are nested, overlapping or distinct) subsume all possible combination of ranges for the value that might be claimed using endpoints of the disclosed ranges. For example, if parameter X is exemplified herein to have values in the range of 1-10 it also describes subranges for Parameter X including 1-9, 1-8, 1-7, 2-9, 2-8, 2-7, 3-9, 3-8, 3-7, 2-8, 3-7, 4-6, or 7-10, 8-10 or 9-10 as mere examples. A range encompasses its endpoints as well as values inside of an endpoint, for example, the range 0-5 includes 0, >0, 1, 2, 3, 4, <5 and 5.

As used herein, the words "preferred" and "preferably" refer to embodiments of the technology that afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the technology. As referred to herein, all compositional percentages are by weight of the total composition, unless otherwise specified. As used herein, the word "include," and its variants, is intended to be non-limiting, such that recitation of items in a list is not to the exclusion of other like items that may also be useful in the materials, compositions, devices, and methods of this technology. Similarly, the terms "can" and "may" and their variants are intended to be non-limiting, such that recitation that an embodiment can or may comprise certain elements or features does not exclude other embodiments of the present invention that do not contain those elements or features.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

Spatially relative terms, such as "under", "below", "lower", "over", "upper", "in front of" or "behind" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

The description and specific examples, while indicating embodiments of the technology, are intended for purposes of illustration only and are not intended to limit the scope of the technology. Moreover, recitation of multiple embodiments having stated features is not intended to exclude other embodiments having additional features, or other embodiments incorporating different combinations of the stated features. Specific examples are provided for illustrative purposes of how to make and use the compositions and methods of this technology and, unless explicitly stated otherwise, are not intended to be a representation that given embodiments of this technology have, or have not, been made or tested.

All publications and patent applications mentioned in this specification are herein incorporated by reference in their entirety to the same extent as if each individual publication or patent application was specifically and individually indicated to be incorporated by reference, especially referenced is disclosure appearing in the same sentence, paragraph, page or section of the specification in which the incorporation by reference appears.

The citation of references herein does not constitute an admission that those references are prior art or have any relevance to the patentability of the technology disclosed herein. Any discussion of the content of references cited is intended merely to provide a general summary of assertions made by the authors of the references, and does not constitute an admission as to the accuracy of the content of such references.

REFERENCES

Abed, R. M., Al-Thukair, A., & de Beer, D. (2006). Bacterial diversity of a cyanobacterial mat degrading petroleum compounds at elevated salinities and temperatures. *FEMS Microbiol. Ecol.* 57(2), 290-301, doi:FEM113 [pii] 10.1111/j.1574-6941.2006.00113.x.

Al-Mueini, R., Al-Dalali, M., Al-Amri, I. S., & Patzelt, H. (2007). Hydrocarbon degradation at high salinity by a novel extremely halophilic actinomycete. *Environ. Chem.* 4(1), 5-7, doi: hypertext transfer protocol available at:// dx.doi.org/10.1071/EN06019.

Al-Thukair, A. A., & Malik, K. (2016). Pyrene metabolism by the novel bacterial strains *Burkholderia fungorum* (T3A13001) and *Caulobacter* sp (T2A12002) isolated from an oil-polluted site in the Arabian Gulf. *Int. Biodeter. Biodegrad.* 110, 32-37, doi: hypertext transfer protocol available at://dx.doi.org/10.1016/j.ibiod.2016.02.005.

Arulazhagan, P., & Vasudevan, N. (2011). Biodegradation of polycyclic aromatic hydrocarbons by a halotolerant bacterial strain *Ochrobactrum* sp. VA1. *Mar. Pollut. Bull.* 62(2), 388-394, doi:S0025-326X(10)00436-4 [pii] 10.1016/j.marpolbul.2010.09.020.

Beyer, A. H., & Palmer, J. (1979). Biological oxidation of dissolved compounds in oilfield-produced water by a pilot aerated lagoon, *J. Petrol. Technol.* 31, 241-245.

Bonfa, M. R., Grossman, M. J., Mellado, E., & Durrant, L. R. (2011). Biodegradation of aromatic hydrocarbons by Haloarchaea and their use for the reduction of the chemical oxygen demand of hypersaline petroleum produced water. *Chemosphere.* 84(11), 1671-1676, doi:S0045-6535 (11)00530-3 [pii] 10.1016/j.chemosphere.2011.05.005.

Bostrom, C. E., Gerde, P., Hanberg, A., Jernstrom, B., Johansson, C., Kyrklund, T., et al. (2002). Cancer risk assessment, indicators, and guidelines for polycyclic aromatic hydrocarbons in the ambient air. *Environ. Health Perspect.* 110 Suppl 3, 451-488, doi:sc271_5_1835 [pii].

Cao, B., Nagarajan, K., & Loh, K. C. (2009). Biodegradation of aromatic compounds: current status and opportunities for biomolecular approaches. *Appl. Microbiol. Biotechnol.* 85(2), 207-228, doi:10.1007/s00253-009-2192-4.

Dastgheib, S. M., Amoozegar, M. A., Khajeh, K., Shavandi, M., & Ventosa, A. (2012). Biodegradation of polycyclic aromatic hydrocarbons by a halophilic microbial consortium. *Appl. Microbiol. Biotechnol.* 95(3), 789-798, doi: 10.1007/s00253-011-3706-4.

Dean-Ross, D., & Cerniglia, C. E. (1996). Degradation of pyrene by *Mycobacterium flavescens. Appl Microbiol Biotechnol.* 46(3), 307-312.

dos Santos, E. V., Bezerra Rocha, J. H., de Araujo, D. M., de Moura, D. C., & Martinez-Huitle, C. A. (2014). Decontamination of produced water containing petroleum hydrocarbons by electrochemical methods: a minireview. [journal article]. *Environmental Science and Pollution Research.* 21(14), 8432-8441, doi:10.1007/s11356-014-2780-4.

Erdoğmuş, S. F., Mutlu, B., Korcan, S. E., Guven, K., & Konuk, M. (2013). Aromatic Hydrocarbon Degradation by Halophilic Archaea Isolated from Camalti Saltern, Turkey. *Water, Air, & Soil Pollution.* 224(3), 1-9, doi: 10.1007/s1270-013-1449-9.

Fakhru'l-Razi, A., Pendashteh, A., Abdullah, L. C., Biak, D. R., Madaeni, S. S., & Abidin, Z. Z. (2009). Review of technologies for oil and gas produced water treatment. *J. Hazard. Mater.* 170(2-3), 530-551, doi:10.1016/ j.jhazmat.2009.05.044S0304-3894(09)00778-X [pii].

Fathepure, B. Z. (2014). Recent studies in microbial degradation of petroleum hydrocarbons in hypersaline environments. *Front Microbiol.* 5, 173, doi:10.3389/ fmicb.2014.00173.

Feitkenhauer, H., & Markl, H. (2003). Biodegradation of aliphatic and aromatic hydrocarbons at high temperatures. *Water Sci. Technol.* 47(10), 123-130.

Feitkenhauer, H., Muller, R., & Markl, H. (2003). Degradation of polycyclic aromatic 445 hydrocarbons and long chain alkanes at 60-70 degrees C. by *Thermus* and *Bacillus* spp [corrected]. *Biodegrad.* 14(6), 367-372.

Garcia, M. T., Mellado, E., Ostos, J. C., & Ventosa, A. (2004). *Halomonas organivorans* sp. nov., a moderate halophile able to degrade aromatic compounds. *Int. J. Syst. Evol. Microbiol.* 54(Pt 5), 1723-1728, doi:10.1099/ ijs.0.63114-054/5/1723 [pii].

Garcia, M. T., Ventosa, A., & Mellado, E. (2005). Catabolic versatility of aromatic compound degrading halophilic bacteria. *FEMS Microbiol. Ecol.* 54(1), 97-109, doi: hypertext transfer protocol available at://dx.doi.org/ 10.1016/j.femsec.2005.03.009.

Habe, H., Kanemitsu, M., Nomura, M., Takemura, T., Iwata, K., Nojiri, H., et al. (2004). Isolation and characterization of an alkaliphilic bacterium utilizing pyrene as a carbon source. *J. Biosci. Bioengineer.* 98(4), 306-308, doi: hypertext transfer protocol available at://dx.doi.org/10.1016/ S1389-1723(04)00287-7.

Habe, H., Kanemitsu, M., Nomura, M., Takemura, T., Iwata, K., Nojiri, H., et al. (2004). Isolation and characterization of an alkaliphilic bacterium utilizing pyrene as a carbon source. *J. Biosci. Bioeng.* 98(4), 306-308, doi:S1389-1723(04)00287-7 [pii] 10.1016/S1389-1723(04)00287-7.

Heitkamp, M. A., Franklin, W., & Cerniglia, C. E. (1988). Microbial metabolism of polycyclic aromatic hydrocarbons: isolation and characterization of a pyrene-degrading bacterium. *Appl. Environ. Microbiol.* 54(10), 2549-2555.

Khan, A. A., Kim, S. J., Paine, D. D., & Cerniglia, C. E. (2002). Classification of a polycyclic aromatic hydrocarbon-metabolizing bacterium, *Mycobacterium* sp. strain PYR-1, as *Mycobacterium vanbaalenii* sp. nov. *Int. J. Syst. Evol. Microbiol.* 52(Pt 6), 1997-2002.

Khemili-Talbi, S., Kebbouche-Gana, S., Akmoussi-Toumi, S., Angar, Y., & Gana, M. L. (2015). Isolation of an extremely halophilic arhaeon *Natrialba* sp. C21 able to degrade aromatic compounds and to produce stable biosurfactant at high salinity. [journal article]. *Extremophiles.* 19(6), 1109-1120, doi:10.1007/s00792-015-0783-9.

Kim, Y. H., Freeman, J. P., Moody, J. D., Engesser, K. H., & Cerniglia, C. E. (2005). Effects of pH on the degradation of phenanthrene and pyrene by *Mycobacterium vanbaalenii* PYR-1. *Appl. Microbiol. Biotechnol.* 67(2), 275-285, doi:10.1007/s00253-004-1796-y.

Klankeo, P., Nopcharoenkul, W., & Pinyakong, O. (2009). Two novel pyrene-degrading *Diaphorobacter* sp. and *Pseudoxanthomonas* sp. isolated from soil. *J Biosci. Bioeng.* 108(6), 488-495, doi:10.1016/j.jbiosc.2009.05.016 S1389-1723(09)00259-X [pii].

Liang, Y., Gardner, D. R., Miller, C. D., Chen, D., Anderson, A. J., Weimer, B. C., et al. (2006). Study of biochemical pathways and enzymes involved in pyrene degradation by *Mycobacterium* sp. Strain KMS. *Appl. Environ. Microbiol.* 72(12), 7821-7828, doi:AEM.01274-06 [pii] 10.1128/AEM.01274-06.

Lu, J., Guo, C., Zhang, M., Lu, G., & Dang, Z. (2014). Biodegradation of single pyrene and mixtures of pyrene by a fusant bacterial strain F14. *Intern. Biodeter. & Biodegrad.* 87, 75-80, doi: hypertext transfer protocol available at://dx.doi.org/10.1016/j.ibiod.2013.11.004.

Ma, J., Xu, L., & Jia, L. (2013). Characterization of pyrene degradation by *Pseudomonas* sp. Strain Jpyr-1 isolated from active sewage sludge. *Bioresour. Technol.* 140, 15-21, doi:10.1016/j.biortech.2013.03.184S0960-8524 (13)00588-9 [pii].

Margesin, R., & Schinner, F. (2001). Biodegradation and bioremediation of hydrocarbons in extreme environments. *Appl. Microbiol. Biotechnol.* 56(5-6), 650-663.

Martins, L. F., & Peixoto, R. S. (2012). Biodegradation of petroleum hydrocarbons in hypersaline environments. *Braz. J. Microbiol.* 43(3), 865-872, doi:10.1590/S1517-83822012000300003 S1517-83822012000300003 [pii].

Meena, S. S., Sharma, R. S., Gupta, P., Karmakar, S., & Aggarwal, K. K. (2016). 490 Isolation and identification of *Bacillus megaterium* YB3 from an effluent contaminated site efficiently degrades pyrene. *J. Basic. Microbiol.* 56(4), 369-378, doi:10.1002/jobm.201500533.

Moscoso, F., Deive, F. J., Longo, M. A., & Sanroman, M. A. (2015). Insights into polyaromatic hydrocarbon biodegradation by *Pseudomonas stutzeri* CECT 930: operation at bioreactor scale and metabolic pathways. [journal article]. *Intern. J. Environm. Sc. Technol.* 12(4), 1243-1252, doi: 10.1007/s13762-014-0498-y.

Munirasu, S., Haija, M. A., & Banat, F. (2016). Use of membrane technology for oil field and refinery produced water treatment—A review. *Proc. Saf. Environ. Protect.* 100, 183-202, doi: hypertext transfer protocol available at://dx.doi.org/10.1016/j.psep.2016.01.010.

Nzila, A. (2013). Update on the cometabolism of organic pollutants by bacteria. *Environ. Pollut.* 178, 474-482, doi:10.1016/j.envpol.2013.03.042S0269-7491(13) 00175-9 [pii].

Nzila, A., Razzak, S., & Zhu, J. (2016). Bioaugmentation: An Emerging Strategy of Industrial Wastewater Treatment for Reuse and Discharge. *Intern. J. Environ. Res. Public Health.* 13(9), 846.

Nzila, A., Thukair, A., Sankara, S., Chanbasha, B., & Musa Musa, M. (2016). Isolation and characterization of naphthalene biodegrading *Methylobacterium radiotolerans* bacterium from the eastern coastline of the Kingdom of Saudi Arabia *Arch. Environ. Prot.* 42, 25.

Oyehan, T. A., & Al-Thukair, A. A. (2017). Isolation and characterization of PAH-degrading bacteria from the Eastern Province, Saudi Arabia. *Mar. Pollut. Bull.* 115(1-2), 39-46, doi:S0025-326X(16)30903-1 [pii] 10.1016/j.marpolbul.2016.11.007.

Sarma, P. M., Duraja, P., Deshpande, S., & Lal, B. (2010). Degradation of pyrene by an enteric bacterium, *Leclercia adecarboxylata* PS4040. *Biodegrad.* 21(1), 59-69, doi: 10.1007/s10532-009-512 9281-z.

Seo, J. S., Keum, Y. S., & Li, Q. X. (2009). Bacterial degradation of aromatic compounds. *Int. J. Environ. Res. Public Health.* 6(1), 278-309, doi:10.3390/ijerph6010278.

Sorokin, D. Y., Janssen, A. J. H., & Muyzer, G. (2012). Biodegradation Potential of Halo(alkali)philic Prokaryotes. *Crit. Rev. Environ. Sc. Technol.* 42(8), 811-856, doi:10.1080/10643389.2010.534037.

Verma, N., Pink, M., Rettenmeier, A. W., & Schmitz-Spanke, S. (2012). Review on proteomic analyses of benzo[a]pyrene toxicity. *Proteomics.* 12(11), 1731-1755, doi:10.1002/pmic.201100466.

Viamajala, S., Peyton, B. M., Richards, L. A., & Petersen, J. N. (2007). Solubilization, solution equilibria, and biodegradation of PAH's under thermophilic conditions. *Chemosphere.* 66(6), 1094-1106, doi:S0045-6535(06) 00819-8 [pii] 10.1016/j.chemosphere.2006.06.059.

Vila, J., Lopez, Z., Sabate, J., Minguillon, C., Solanas, A. M., & Grifoll, M. (2001). Identification of a novel metabolite in the degradation of pyrene by *Mycobacterium* sp. strain AP1: actions of the isolate on two- and three-ring polycyclic aromatic hydrocarbons. *Appl Environ Microbiol.* 67(12), 5497-5505, doi:10.1128/AEM.67.12.5497-5505.2001.

Wang, B., Lai, Q., Cui, Z., Tan, T., & Shao, Z. (2008). A pyrene-degrading consortium from deep-sea sediment of the West Pacific and its key member *Cycloclasticus* sp. P1. *Environ. Microb.* 10(8), 1948-1963, doi:10.1111/j.1462-2920.2008.01611.x.

Wang, F., Liu, Y., Tang, Z., Hou, M., Wang, C., Wang, X., et al. (2017). Simultaneous determination of 15 phthalate esters in commercial beverages using dispersive liquid-liquid microextraction coupled to gas chromatography-mass spectrometry. [10.1039/C7AY00123A]. *Anal. Methods.* 9(12), 1912-1919, doi:10.1039/c7ay00123a.

Wang, S., Li, X., Liu, W., Li, P., Kong, L., Ren, W., et al. (2012). Degradation of pyrene by immobilized microorganisms in saline-alkaline soil. *J Environ Sci* (China). 24(9), 1662-1669.

Wang, Y. N., Cai, H., Chi, C. Q., Lu, A. H., Lin, X. G., Jiang, Z. F., et al. (2007). *Halomonas shengliensis* sp. nov., a moderately halophilic, denitrifying, crude-oil-utilizing bacterium. *Int. J. Syst. Evol. Microbiol.* 57(Pt 6), 1222-1226, doi:10.1099/ijs.0.64973-0.

Yuan, J., Lai, Q., Wang, B., Sun, F., Liu, X., Du, Y., et al. (2009). *Oceanicola pacificus* sp. nov., isolated from a deep-sea pyrene-degrading consortium. *Int. J. Syst. Evol. Microbiol.* 59(5), 1158-1161, 540 doi:doi:10.1099/ijs.0.003400-0.

Zeinali, M., Vossoughi, M., & Ardestani, S. K. (2008a). Degradation of phenanthrene and anthracene by *Nocardia otitidiscaviarum* strain TSH1, a moderately thermophilic bacterium. *J. Appl. Microbiol.* 105(2), 398-406, doi: 10.1111/j.1365-2672.2008.03753.x JAM3753 [pii].

Zeinali, M., Vossoughi, M., & Ardestani, S. K. (2008b). Naphthalene metabolism in *Nocardia otitidiscaviarum* strain TSH1, a moderately thermophilic microorganism. *Chemosphere.* 72(6), 905-909, doi:S0045-6535(08) 00408-6 [pii] 10.1016/j.chemosphere.2008.03.038.

Zhou, H., Wang, H., Huang, Y., & Fang, T. (2016). Characterization of pyrene degradation by halophilic *Thalassospira* sp. strain TSL5-1 isolated from the coastal soil of Yellow Sea, China. *Int. Biodeter. Biodegrad.* 107, 62-69, doi: hypertext transfer protocol available at://dx.doi.org/10.1016/j.ibiod.2015.10.022.

The invention claimed is:

1. A method for degrading a polycyclic aromatic compound (PAH) comprising:

pumping groundwater or other liquid contaminated with one or more PAHs into a bioreactor to which one or more bacteria of the genus *Halomonas* have been added, contacting said groundwater or other liquid in the bioreactor with the one or more bacteria in a medium containing NaCl at a temperature of at least 15° C. for a time sufficient to degrade the PAH;

wherein said *Halomonas* have 16s ribosomal RNA that is at least 95% identical to SEQ ID NO: 1.

2. The method of claim 1, wherein said contacting occurs at a pH of less than pH 7 and at a temperature of at least 25° C. and in the presence of at least 5 wt % NaCl and the PAH comprises pyrene.

3. The method of claim 1, wherein said contacting occurs at a pH of at least 7 in a groundwater or other liquid solution at a temperature of at least 25° C. and in the presence of at least 5 wt % NaCl.

4. The method of claim 1, wherein the PAH is pyrene (PYR).

5. The method of claim 1, wherein the PAH is naphthalene (NAPH), anthracene (ANT), or phenanthrene (PHEN).

6. The method of claim 1, wherein said contacting occurs in an aqueous solution at a temperature of at least 37° C.

7. The method of claim 1, wherein the contacting occurs in an aqueous solution containing at least 10 wt. % NaCl.

8. The method of claim 1, wherein said contacting occurs in the presence of pyrene at an acidic pH and at a temperature ranging from 25 to 37° C. and the NaCl is present in an amount of 10-20 wt. % to form a mixture comprising 4-phenanthrenecarboxylic acid, 4-(1-hydroxynaphthalen-2-yl)-2-oxo but-3-enoic acid, and phthalic acid.

9. The method of claim 1, wherein the *Halomonas* is attached to a carrier.

10. The method of claim 1, further comprising providing one or more non-PAH carbon sources for *Halomonas* during said contacting.

11. The method of claim 1, wherein said bioreactor comprises a system of mechanical or electronic elements that process and control the flow and exposure of a material containing a PAH to the *Halomonas* bacteria.

12. The method of claim 1, wherein said groundwater or other liquid is contained in soil, sludge or in or on another solid or semisolid material.

13. The method of claim 1, wherein said contacting occurs in a biopile which is heated electrically.

14. The method of claim 1, further comprising:

contacting the PAH with *Halomonas smyrnensis* having 16s ribosomal RNA that is at least 95% identical to SEQ ID NO: 2 and that degrades PAH and/or with *Idiomarina piscisalsi* having 16s ribosomal RNA-encoding DNA sequence that is at least 95% identical to SEQ ID NO: 4 and that degrades PAH.

15. The method of claim 1, further comprising growing the *Halomonas* in an artificial culture medium to a titer of at least $10^6$ CFU/ml prior to adding to the bioreactor.

16. The method of claim 1, wherein said *Halomonas* have a doubling time of no more than 24 hours in a medium containing 50 ppm pyrene.

17. The method of claim 1, wherein said groundwater or contaminated liquid further contains or is admixed with at least one of crude oil, diesel fuel or lubricating oil.

18. The method of claim 1, wherein said groundwater or contaminated liquid further contains or is admixed with at least one of octane, decane, hexadecane, methylcyclopentane, methylcyclohexane, heptamethylnonane, benzene, toluene, ethylbenzene, m-, o- and p-xylenes, and carbazole.

19. The method of claim 1, wherein said *Halomonas* is mixed with a carrier or bulking agent selected from the group consisting of agricultural waste, tree litter, grain or maize husks or cobs, bagasse, bark, post peelings, fruit waste, stones, or a mixture thereof.

* * * * *

SEQUENCE LISTING

<160> NUMBER OF SEQ ID NOS: 5

<210> SEQ ID NO 1
<211> LENGTH: 1461
<212> TYPE: DNA
<213> ORGANISM: Halomonas shengliensis
<220> FEATURE:
<221> NAME/KEY: misc_feature
<222> LOCATION: (1)..(1461)
<223> OTHER INFORMATION: Halomonas shengliensis strain 10PY-2B 16S ribosomal RNA gene, partial sequence. KU30825.1. Strain 10 PY 2B.

<400> SEQUENCE: 1
gctcagattg aacgctggcg gcaggcctaa cacatgcaag tcgagcggaa acgatcctag 60
cttgctagga ggcgtcgagc ggcggacggg tgagtaacgc ataggaatct gcccggtagt 120
gggggatacc tggggaaacc caggctaata ccgcatacgt cctacgggag aaagcagggg 180
ctcttcggac cttgcgctat cggatgagcc tatgtcggat tagctggttg gtgaggtaat 240
ggctcaccaa ggcgcgatcc gtagctggtc tgagaggatg atcagccaca tcgggactga 300
gacacggccc gaactcctac gggaggcagc agtggggaat attggacaat gggcgcaagc 360
ctgatccagc catgccgcgt ggtgaagaag gccctcgggt tgtaaagcac tttcagtggg 420
gaagaaatcc tcggggctaa taccctcgag ggaggacatc acccacagaa gaagcaccgg 480
ctaactccgt gccagcagcc gcggtaatcg gagggtgcga gcgttaatcg gaattactgg 540
gcgtaaagcg cgcgtaggcg gcctgataag ccggttgtga aagccccggg ctcaacctgg 600
gaacggcatc cggaactgtc aggctagagt gcagggagga aggtagaatt cccggtgtag 660
cggtgaaatg cgtagagatc gggaggaata ccagtggcga aggcggcctt ctggactgac 720
actgacgctg aggtgcgaaa gcgtgggtag caaacaggat taataccctg gtagtccacg 780
ccgtaaacga tgtcgactag ccgttggggt ccttgagacc tttgtggcgc agttaacgcg 840
ataagtcgac cgcctgggga gtacggccgc aaggttaaaa ctcaaatgaa ttgacggggg 900
cccgcacaag cggtggagca tgtggttaat tcgatgcaac gcgaagaacc ttacctaccc 960
ttgacatcga gagaacttgg cagagatgcc ttggtgcctt cgggaactct cagacaggtg 1020
ctgcatggcc gtcgtcagct cgtgttgtga aatttgggtt aagtcccgta acgagcgcaa 1080
cccttgtccc tatttgccag cgattcggtc gggaactcta gggagactgc cggtgacaaa 1140
ccggaggaag gtggggacga cgtcaggtca tcatggccct acgggtaggg ctacacacgt 1200
gctacaatgg ccggtacaaa gggttgcgaa gccgcgaggt ggagccaatc ccgaaaagcc 1260
ggtctcagtc cggatcggag tctgcaactc gactccgtga agtcggatcg ctagtaatcg 1320
tgaatcagaa tgtcacggtg aatacgttcc cgggccttgt acacaccgcc cgtcacacca 1380
tgggagtgga ctgcaccaga agtggttagc ctaacttcgg agggcgatca ccacgtgtgg 1440
ttcatgactg gggtgaagtc g 1461

<210> SEQ ID NO 2

<211> LENGTH: 1267
<212> TYPE: DNA
<213> ORGANISM: Halomonas smyrnensis
<220> FEATURE:
<221> NAME/KEY: misc_feature
<222> LOCATION: (1)..(1267)
<223> OTHER INFORMATION: Halomonas smyrnensis strain 20PY-1B 16S ribosomal RNA gene, partial sequence. KU308252.1. Strain 20 PY 1A.

<400> SEQUENCE: 2

```
tgcgctatcg gatgagccta tgtcggatta gctagttggt gaggtaatgg ctcaccaagg     60

ccgcgatccg tagctggtct gagaggatga tcagccacat cgggactgag acacggcccg    120

aactcctcgg gaggcagcag tggggaatat tggacaatgg gcgaaagcct gatccagcca    180

tgccgcgtgt gtgaagaagg ccttcgggtt gtaaagcact ttcagcgagg aagaacgctt    240

gtgggttaat acccgcaaga aggacatcac tcgcagaaga agcaccggct aactccgtgc    300

cagcagccgc ggtaatacgg agggtgcaag cgttaatcgg aattactggg cgtaaagcgc    360

gcgtaggcgg cttgataagc cgttgtgaaa gccccgggct caacctggga acggcatccg    420

gaactgtcag gctagagtgc aggagaggaa ggtagaattc ccggtgtagc ggtgaaatgc    480

gtagagatcg ggaggaatac cagtggcgag ggcggccttc tggactgaca ctgacgctga    540

ggtggaaagc gtgggtagca aacaggatta gataccctgg tagtccacgc cgtaaacgat    600

gtcgactagc cgttggggtc ctcgaaacct tggggcgcag ttaacgcgat aagtcgaccg    660

cctggggagt acggccgcaa ggttaaaact caaatgaatt gacgggggcc cgcacaagcg    720

gtggagcatg tggtttaatt cgatgcaacg cgagaacctt acctactctt gacatcgagc    780

gaactttcca gagatggatt ggtgccttcg ggaacgctca gacaggtgct gcatggccgt    840

cgtcagctcg tgttgtgaaa tgttgggtta agtcccgtac gagcgcaacc cttgtcccta    900

tttgccagcg attcggtcgg gaactctagg gagactgccg gtgacaaacc ggaggaaggt    960

ggggacgacg tcaggtcatc atggccctta cgagtagggc tacacagtgc tacaatggcc   1020

ggtacaatgg gctgcaatcc cgcgaggggg agctaatctc ataaagccgg tctcagtccg   1080

gatcggagtc tgcaactcga ctccgtgaag tcggaatcgc tagtaatcgt gcacagaatg   1140

gcacggtgaa tacgttcccg ggccttgtac acaccgcccg tcacaccatg ggagtggact   1200

gcaccagaag tggttagcct aacttcggag ggcgatcacc acggtgtggt tcatgactgg   1260

gtgaagt                                                             1267
```

<210> SEQ ID NO 3
<211> LENGTH: 1499
<212> TYPE: DNA
<213> ORGANISM: Halomonas xianhensis
<220> FEATURE:
<221> NAME/KEY: misc_feature
<222> LOCATION: (1)..(1499)
<223> OTHER INFORMATION: Halomonas xianhensis strain A-1 16S ribosomal RNA gene, partial sequence. GI: 636559956. Strain A1.

<400> SEQUENCE: 3

```
agagtttgat cctggctcag attgaacgct ggcggcaggc ctaacacatg caagtcgagc     60

ggcagcggga ggtgcttgca cctcgccggc gagcggcgga cgggtgagta atgcatagga    120

aactgcccgg tagtggggga taacctgggg aaacccaggc taataccgca tacgtcctac    180

gggagaaagc aggggctctt cggaccttgc gctatcggat gtgcctatgt cggattagct    240

ggttggtgag gtaacggctc accaaggcga cgatccgtag ctggtctgag aggatgatca    300
```

```
gccacactgg gactgagaca cggcccagac tcctacggga ggcagcagtg gggaatattg    360

gacaatgggc gaaagcctga tccagccatg ccgcgtgtgt gaagaaggct ttcgggttgt    420

aaagcacttt cagtggggaa gaaagcctgg cggttaatac ccgtcaggga cgacatcacc    480

cacagaagaa gcaccggcta actccgtgcc agcagccgcg gtaatacgga gggtgcgagc    540

gttaatcgga attactgggc gtaaagcgcg cgtaggcggc ttgataagcc gggtgtgaaa    600

gccctgggct caacctggga acggcatccg gaactgtcaa gctagagtgc aggagaggaa    660

ggtagaattc ccggtgtagc ggtgaaatgc gtagagatcg ggaggaatac cagtggcgaa    720

ggcggccttc tggactgaca ctgacgctga ggtgcgaaag cgtgggtagc aaacaggatt    780

agataccctg gtagtccacg ccgtaaacga tgtcgactag ccgttgggct cctcgcgagc    840

ttagtggcgc agttaacgcg ataagtcgac cgcctgggga gtacggccgc aaggttaaaa    900

ctcaaatgaa ttgacggggg cccgcacaag cggtggagca tgtggtttaa ttcgatgcaa    960

cgcgaagaac cttacctacc cttgacatcc tcggaatccg ccggagacgg cggagtgcct   1020

tcgggaaccg agtgacaggt gctgcatggc tgtcgtcagc tcgtgttgtg aaatgttggg   1080

ttaagtcccg taacgagcgc aacccttgtc cctatttgcc agcgattcgg tcgggaactc   1140

tagggagact gccggtgaca aaccggagga aggtggggac gacgtcaagt catcatggcc   1200

cttacgggta gggctacaca cgtgctacaa tggcaggtac aaagggtcgc aagacggcga   1260

cgtggagcta atcccagaaa gcctgcctca gtccggattg gagtctgcaa ctcgactcca   1320

tgaagtcgga atcgctagta atcgtgaatc agaatgtcac ggtgaatacg ttcccgggcc   1380

ttgtacacac cgcccgtcac accatgggag tggactgcac cagaagtggt tagcctaact   1440

tcggagggcg atcaccacgg tgtggttcat gactggggtg aagtcgtaac aaggtaacc    1499
```

<210> SEQ ID NO 4
<211> LENGTH: 1478
<212> TYPE: DNA
<213> ORGANISM: Idiomarina piscisalsi
<220> FEATURE:
<221> NAME/KEY: misc_feature
<222> LOCATION: (1)..(1478)
<223> OTHER INFORMATION: Idiomarina sp. 10PY-1A 16S ribosomal RNA gene, partial sequence GenBank: KU308250.1

<400> SEQUENCE: 4

```
ctcagattga acgctggcgg caggcctaac acatgcaagt cgagcggtaa cagagagaag     60

cttgcttctc tgctgacgag cggcggacgg gtgagtaata cttgggaatt tgcctttagg    120

cgggggaaac cactggaaac ggtggctaat accgcataat gtctacggac caaagtgggg    180

gaccttcggg cctcacacct aaagatgagc ccaagcggga ttagctagtt ggtgaggtaa    240

aggctcacca aggcacgatc cctagctgtt ctgagaggat gatcagccac actgggactg    300

agacacggcc cagactccta cgggaggcag cagtggggaa tattgcacaa tgggcgcaag    360

cctgatgcag ccatgccgcg ttgtgaagaa ggccttcggg ttgtaaagca ctttcagtgg    420

tgaggaaagg gtgatagtta atagcgatca cagttgacgt tagccacaga agaagcaccg    480

gctaactccg tgccagcagc cgcggtaaac ggagggtgca agcgttaatc ggaattactg    540

ggcgtaaagc gtacgtaggc ggtgtgttaa gctagatgtg aaagccccgg gctcaacctg    600

ggaattgcat ttagaactgg cacgctagag tcctgagagg gtggtagaat ttccagtgta    660

gcggtgaaat gcgtagatat tggaaggaat accggtggcg aaggcggcca cctggtcaga    720

gactgacgct gaggtacgaa agcgtgggga gcaaacagga ttgataccct ggtagtccac    780
```

```
gccgtaaacg atgtcaacta gttgttcgtg tcattaagac gtgagtaacg cagctaacgc     840

actaagtgaa ccccctgggg agtacggccg caaggttaaa actcaaatga attgacgggg     900

gcccgcacaa gcggtggagc atgtggttaa ttcgatgcaa cgcgaagaac cttaccatcc     960

cttgacatcc agtgaatttt ccagagatgg attagtgcct tcgggaacac tgagacaggt    1020

gctgcatggc tgtcgtcagc tcgtgttgtg agatttgggt taagtcccgc aacgagcgca    1080

acccttatcc ttagttgcca gcggttcggc cgggaactct ggggagactg ccggtgataa    1140

accggaggaa ggtggggacg acgtcaagtc atcatggccc tacgggatgg gctacacacg    1200

tgctacaatg gcgcgtacaa agggcagcga acctgcgagg gtaagcgaat ctcataaagc    1260

gcgtcgtagt ccggattgga gtctgcaact cgactccatg aagtcggatc gctagtaatc    1320

gtggatcaga atgccacggt gaatacgttc ccgggccttg tacacaccgc ccgtcacacc    1380

atgggagtgg gctgcaccag aagtggttag tttaaccttc gggagaacga tcacccggtg    1440

tggttcatga ctggggtgaa gtcgtacagg gaaaaccc                            1478


<210> SEQ ID NO 5
<211> LENGTH: 1499
<212> TYPE: DNA
<213> ORGANISM: Halomonas xianhensis
<220> FEATURE:
<221> NAME/KEY: misc_feature
<222> LOCATION: (1)..(1499)
<223> OTHER INFORMATION: Halomonas xianhensis strain A-1 16S ribosomal
      RNA gene partial sequence NCBI Reference Sequence
      NR_116016.1.GI:636559956

<400> SEQUENCE: 5

agagtttgat cctggctcag attgaacgct ggcggcaggc ctaacacatg caagtcgagc      60

ggcagcggga ggtgcttgca cctcgccggc gagcggcgga cgggtgagta atgcatagga     120

aactgcccgg tagtggggga taacctgggg aaacccaggc taataccgca tacgtcctac     180

gggagaaagc aggggctctt cggaccttgc gctatcggat gtgcctatgt cggattagct     240

ggttggtgag gtaacggctc accaaggcga cgatccgtag ctggtctgag aggatgatca     300

gccacactgg gactgagaca cggcccagac tcctacggga ggcagcagtg gggaatattg     360

gacaatgggc gaaagcctga tccagccatg ccgcgtgtgt gaagaaggct ttcgggttgt     420

aaagcacttt cagtggggaa gaaagcctgg cggttaatac ccgtcaggga cgacatcacc     480

cacagaagaa gcaccggcta actccgtgcc agcagccgcg gtaatacgga gggtgcgagc     540

gttaatcgga attactgggc gtaaagcgcg cgtaggcggc ttgataagcc gggtgtgaaa     600

gccctgggct caacctggga acggcatccg gaactgtcaa gctagagtgc aggagaggaa     660

ggtagaattc ccggtgtagc ggtgaaatgc gtagagatcg ggaggaatac cagtggcgaa     720

ggcggccttc tggactgaca ctgacgctga ggtgcgaaag cgtgggtagc aaacaggatt     780

agataccctg gtagtccacg ccgtaaacga tgtcgactag ccgttgggct cctcgcgagc     840

ttagtggcgc agttaacgcg ataagtcgac cgcctgggga gtacggccgc aaggttaaaa     900

ctcaaatgaa ttgacggggg cccgcacaag cggtggagca tgtggtttaa ttcgatgcaa     960

cgcgaagaac cttacctacc cttgacatcc tcggaatccg ccggagacgg cggagtgcct    1020

tcgggaaccg agtgacaggt gctgcatggc tgtcgtcagc tcgtgttgtg aaatgttggg    1080

ttaagtcccg taacgagcgc aacccttgtc cctatttgcc agcgattcgg tcgggaactc    1140

tagggagact gccggtgaca aaccggagga aggtggggac gacgtcaagt catcatggcc    1200

cttacgggta gggctacaca cgtgctacaa tggcaggtac aaagggtcgc aagacggcga    1260
```

-continued

```
cgtggagcta atcccagaaa gcctgcctca gtccggattg gagtctgcaa ctcgactcca   1320

tgaagtcgga atcgctagta atcgtgaatc agaatgtcac ggtgaatacg ttcccgggcc   1380

ttgtacacac cgcccgtcac accatgggag tggactgcac cagaagtggt tagcctaact   1440

tcggagggcg atcaccacgg tgtggttcat gactggggtg aagtcgtaac aaggtaacc    1499
```

UNITED STATES PATENT AND TRADEMARK OFFICE
CERTIFICATE OF CORRECTION

PATENT NO. : 10,478,652 B2
APPLICATION NO. : 15/843809
DATED : November 19, 2019
INVENTOR(S) : Alexis Mouanda Nzila et al.

Page 1 of 1

It is certified that error appears in the above-identified patent and that said Letters Patent is hereby corrected as shown below:

On the Title Page

Item (73), the Assignee's name is incorrect. Item (73) should read:
--(73) Assignees: KING FAHD UNIVERSITY OF PETROLEUM AND MINERALS, Dhahran (SA)--

Signed and Sealed this
Twenty-fifth Day of February, 2020

Andrei Iancu
*Director of the United States Patent and Trademark Office*